US008574572B2

(12) United States Patent
Crump et al.

(10) Patent No.: US 8,574,572 B2
(45) Date of Patent: Nov. 5, 2013

(54) METHOD OF TREATING PULMONARY DISEASE BY ADMINISTERING AN ANTIBODY TO G-CSF RECEPTOR

(75) Inventors: David Eric Crump, Balwyn North (AU); Andrew Donald Nash, Kew (AU)

(73) Assignee: CSL Limited, Parkville, Victoria (AU)

( * ) Notice: Subject to any disclaimer, the term of this patent is extended or adjusted under 35 U.S.C. 154(b) by 141 days.

(21) Appl. No.: 12/377,256

(22) PCT Filed: Aug. 10, 2007

(86) PCT No.: PCT/AU2007/001127
§ 371 (c)(1),
(2), (4) Date: Jun. 9, 2009

(87) PCT Pub. No.: WO2008/017126
PCT Pub. Date: Feb. 14, 2008

(65) Prior Publication Data
US 2009/0324591 A1    Dec. 31, 2009

(30) Foreign Application Priority Data

Aug. 11, 2006   (AU) ................................ 2006904378

(51) Int. Cl.
*A61K 39/395*    (2006.01)
(52) U.S. Cl.
USPC .................. 424/130.1; 424/133.1; 424/141.1; 424/143.1
(58) Field of Classification Search
None
See application file for complete search history.

(56) References Cited

FOREIGN PATENT DOCUMENTS

| JP | 2005-536535 A | 12/2005 |
|---|---|---|
| WO | 2006/077501 A2 | 7/2006 |
| WO | 2007/084485 | 7/2007 |

OTHER PUBLICATIONS

Chuntharapai et al (1997) Method on Enzymology, vol. 288, pp. 15-27.*
de Bruin et al (2010), Experimental Hematology, vol. 38, pp. 1022-1035.*
Beers & Berkow Editors, The Merck Manual (1999), 17th edition, pp. 986-995.*
Bozinvski et al, "Granulocyte/macrophage-colony-stimulating factor (GM-CSF) regulates lung innate immunity to lipolysaccharide through Akt/Erk activation of NF[kappa]B and AP-1 in vivo," Journal of Biological Chemistry, Nov. 8, 2002, 277(45): 42808-42814.
Sato et al, "Smoke extract stimulates lung fibroblasts to release neutrophil and monocyte chemotactic activities," American Journal of Physiology, Dec. 1999, 277(6) part 1: L1149-L1157.
Masubuchi et al, "Smoke extract stimulates lung epithelial cells to release neutrophil and monocyte chemotactic activity," American Journal Pathology, Dec. 1998, 153(6): 1903-1912.
Koyama et al, "Alveolar type II-like cells release G-CSF as neutrophil chemotactic activity," American Journal of Physiology, Lung Cellular and Molecularphysiology, Oct. 1, 1998, 275(4): L687-L693.
Yousefi et al, "cDNA representational difference analysis of human neutrophils stimulated by GM-CSF," Biochemical and Biophysical Research Communication, Oct. 22, 2000, 277(2):401-409.
Takafuji et al, "Matrix metalloproteinase-9 release from human leukocytes," Journal of Investigation Allergology & Clinical Immunology, 2003, 13(1): 50-55.
Yong et al, "Granulocyte Colony-Stimulating Factor (F-CSF) Increases Neutrophil Migration Across Vascular Endothelium Independent of an Effect on Adhesion: Comparison with Granulocyte-Marcophage Colony-Stimulating Factor (GM-CSF)," British Journal of Haematology, Mar. 19, 1996, 94(1):40-47.
Parnham et al, "Modulation of neutrophil and inflammation markers in chronic obstructive pulmonary disease by short-term azithromycin treatment" European Journal of Pharmacology, Elsevier, Jul. 4, 2005, 517 (1-2):132-143.
Puljic et al, "Lipopolysaccharide-induced lung inflammation is inhibited by neutralization of GM-CSF" European Journal of Pharmacology, Elsevier, Feb. 3, 2007, 557(2-3):230-235.
Vlahos et al, "Therapeutic potential of treating chronic obstructive pulmonary disease (COPD) by neutralising granulocyte macrophage-colony stimulating factor (GM-CSF)" Pharmacology and Therapeutics, Elsevier, Oct. 1, 2006, 112(1):106-115.
Knapp et al, "Activation of Neutrophils and Inhibition of the Proinflammatory Cytokine Response by Endogenous Granulocyte Colony-Stimulating Factor in Murine Pneumococcal Pneumonia," The Journal of Infectious Disease, 2004, 189(8): 1506-1515.
Nishimaki et al, "Neutrophil survival-enhancing activity in sputum from patient with diffuse panbronchiolitis," Respiratory Medicine, 2005, 99(7):910-917.
Koyama et al, "Cyclophosphamide stimulates lung fibroblasts to release neutrophil and monocyte chemoattractants" American Journal of Physiology—Lung Cellular and Molecular Physiology, 2001, 280(60): L1203-L1211.
European Search Report, EP 07 78 4767, Mar. 1, 2010.
Katsushi Nishimaki et al.; Neutrophil survival-enhancing activity in sputum from patients with diffuse panbronchiolitis; Respiratory Medicine, 2005; p. 910-917; Elsevier Ltd.
Sekiya Koyama et al.; Cyclophosphamide stimulates lung fibroblasts to release neutrophil and monocyte chemoattractants; Am J Physiol Lung Cell Mol Physiol; 2001; vol. 280; p. 1203-L1211; The American Physiological Society.
Sylvia Knapp et al.; Activation of Neutrophils and Inhibition of the Proinflammatory Cytokine Response by Endogenous Granulocyte Colony-Stimulating Factor in Murine Pneumococcal Pneumonia; The Journal of Infectious Diseases. 2004, vol. 189, No. 8, pp. 1506-1515.
Layton et al., Neutralising Antibodies to the Granulocyte Colony-stimulating Factor Receptor Recognise both the Immunoglobulin-like Domain and the Cytokine Receptor Homologous Domain, Growth Factors, 1997, pp. 117-130, vol. 14.

(Continued)

*Primary Examiner* — Prema Mertz
(74) *Attorney, Agent, or Firm* — Scully, Scott, Murphy & Presser, P.C.

(57) ABSTRACT

The present invention relates generally to a method for treating or preventing or otherwise ameliorating the effects of pulmonary diseases characterized by or associated with infiltration of neutrophils and complications arising therefrom. The present invention further provides agents and pharmaceutical compositions comprising agents which inhibit the activity of G-CSF or its receptor, interfere with G-CSF signaling and/or which down-regulate expression of G-CSF or its receptor.

8 Claims, 19 Drawing Sheets

(56) References Cited

OTHER PUBLICATIONS

Linden et al., Neutrophilic airway inflammation and IL-17, Allergy, 2002, pp. 769-775, vol. 57.
Barnes, Neutrophils Find Smoke Attractive, Science Magazine, Perspectives, Medicine, Oct. 1, 2010, pp. 40-41, vol. 330, www.sciencemag.org.
Shapiro, Steven D., "Animal Models for Chronic Obstructive Pulmonary Disease," American Journal of Respiratory Cell and Molecular Biology (2000), vol. 22, pp. 4-7.
http://web.jhu.edu/Biswal/exposure_core/copd.html, CPOD Exposure Facility, 5 pages, accessed on Jun. 6, 2012.
Ishii, T., et al., "Recent progress on the therapy for chronic obstructive pulmonary disease (COPD)—Usefulness and practice of the step-by-step pharmacologic therapy", Nippon Rinsho, 57:105-110 (1999) (English language abstract).
Notice of Reasons for Rejection dated Aug. 13, 2012 for Japanese Patent Application No. 2009-523112 (English language translation only).
European Office Action dated Oct. 26, 2012 for Application No. EP 12 17 4059.
Metcalf, D., "The colony-stimulating factors and cancer", Nature Reviews, p. 425-434, 10(6):Jun. 2010.
deBoer, W. I., "Cytokines and Therapy in CPOD*: A Promising Combination?", Chest, p. 209S-218S, 121(5): May 2002.
European Office Action dated Jan. 25, 2012 for European Application No. 07 784 767.1.

* cited by examiner (a)

(b)

(c)

(d)

SEQUENCE LISTING

<160> NUMBER OF SEQ ID NOS: 8

<210> SEQ ID NO 1
<211> LENGTH: 204

<212> TYPE: PRT
<213> ORGANISM: Homo sapiens

<400> SEQUENCE: 1

```
Met Ala Gly Pro Ala Thr Gln Ser Pro Met Lys Leu Met Ala Leu Gln
1               5                   10                  15
Leu Leu Leu Trp His Ser Ala Leu Trp Thr Val Gln Glu Ala Thr Pro
            20                  25                  30
Leu Gly Pro Ala Ser Ser Leu Pro Gln Ser Phe Leu Leu Lys Cys Leu
        35                  40                  45
Glu Gln Val Arg Lys Ile Gln Gly Asp Gly Ala Ala Leu Gln Glu Lys
    50                  55                  60
Leu Cys Ala Thr Tyr Lys Leu Cys His Pro Glu Glu Leu Val Leu Leu
65                  70                  75                  80
Gly His Ser Leu Gly Ile Pro Trp Ala Pro Leu Ser Ser Cys Pro Ser
                85                  90                  95
Gln Ala Leu Gln Leu Ala Gly Cys Leu Ser Gln Leu His Ser Gly Leu
            100                 105                 110
Phe Leu Tyr Gln Gly Leu Leu Gln Ala Leu Glu Gly Ile Ser Pro Glu
        115                 120                 125
Leu Gly Pro Thr Leu Asp Thr Leu Gln Leu Asp Val Ala Asp Phe Ala
    130                 135                 140
Thr Thr Ile Trp Gln Gln Met Glu Glu Leu Gly Met Ala Pro Ala Leu
145                 150                 155                 160
Gln Pro Thr Gln Gly Ala Met Pro Ala Phe Ala Ser Ala Phe Gln Arg
                165                 170                 175
Arg Ala Gly Gly Val Leu Val Ala Ser His Leu Gln Ser Phe Leu Glu
            180                 185                 190
Val Ser Tyr Arg Val Leu Arg His Leu Ala Gln Pro
        195                 200
```

<210> SEQ ID NO 2
<211> LENGTH: 1498
<212> TYPE: DNA
<213> ORGANISM: Homo sapiens

<400> SEQUENCE: 2

| | | | |
|---|---|---|---|
| ggagcctgca gcccagcccc acccagaccc atggctggac ctgccaccca gagccccatg | 60 |
| aagctgatgg ccctgcagct gctgctgtgg cacagtgcac tctggacagt gcaggaagcc | 120 |
| accccctgg gcctgccag ctccctgccc agagcttcc tgctcaagtg cttagagcaa | 180 |
| gtgaggaaga tccagggcga tggcgcagcg ctccaggaga agctgtgtgc cacctacaag | 240 |
| ctgtgccacc ccgaggagct ggtgctgctc ggacactctc tgggcatccc ctgggctccc | 300 |
| ctgagcagct gccccagcca ggccctgcag ctggcaggct gcttgagcca actccatagc | 360 |
| ggccttttcc tctaccaggg gctcctgcag gccctggaag gcatctcccc cgagttgggt | 420 |
| cccaccttgg acacactgca gctggacgtc gccgactttg ccaccaccat ctggcagcag | 480 |
| atggaagaac tgggaatggc ccctgccctg cagcccaccc aggtgccat gccggccttc | 540 |
| gcctctgctt tccagcgccg ggcaggaggg gtcctagttg cctcccatct gcagagcttc | 600 |
| ctggaggtgt cgtaccgcgt tctacgccac cttgcccagc cctgagccaa gccctcccca | 660 |
| tcccatgtat ttatctctat ttaatattta tgtctattta agcctcatat ttaaagacag | 720 |
| ggaagagcag aacggagccc caggcctctg tgtccttccc tgcatttctg agtttcattc | 780 |
| tcctgcctgt agcagtgaga aaaagctcct gtcctcccat cccctggact gggaggtaga | 840 |

-continued

```
taggtaaata ccaagtattt attactatga ctgctcccca gccctggctc tgcaatgggc      900
actgggatga gccgctgtga gccctggtc ctgagggtcc ccacctggga cccttgagag       960
tatcaggtct cccacgtggg agacaagaaa tccctgttta atatttaaac agcagtgttc    1020
cccatctggg tccttgcacc cctcactctg gcctcagccg actgcacagc ggcccctgca    1080
tccccttggc tgtgaggccc ctggacaagc agaggtggcc agagctggga ggcatggccc    1140
tggggtccca cgaatttgct ggggaatctc gttttcttc ttaagacttt tgggacatgg     1200
tttgactccc gaacatcacc gacgcgtctc ctgtttttct gggtggcctc gggacacctg    1260
ccctgccccc acgagggtca ggactgtgac tcttttagg gccaggcagg tgcctggaca     1320
tttgccttgc tggacgggga ctggggatgt gggagggagc agacaggagg aatcatgtca    1380
ggcctgtgtg tgaaaggaag ctccactgtc accctccacc tcttcaccc ccactcacca     1440 gtgtcccctc cactgtcaca ttgtaactga acttcaggat aataaagtgc ttgcctcc      1498
```

<210> SEQ ID NO 3
<211> LENGTH: 525
<212> TYPE: DNA
<213> ORGANISM: Homo sapiens

<400> SEQUENCE: 3

```
acccccctgg gccctgccag ctccctgccc cagagcttcc tgctcaagtg cttagagcaa      60
gtgaggaaga tccagggcga tggcgcagcg ctccaggaga agctgtgtgc cacctacaag    120
ctgtgccacc ccgaggagct ggtgctgctc ggacactctc tgggcatccc ctgggctccc    180
ctgagcagct gccccagcca ggccctgcag ctggcaggct gcttgagcca actccatagc    240
ggccttttcc tctaccaggg gctcctgcag gccctggaag ggatctcccc cgagttgggt    300
cccaccttgg acacactgca gctggacgtc gccgactttg ccaccaccat ctggcagcag    360
atggaagaac tgggaatggc ccctgccctg cagcccaccc agggtgccat gccggccttc    420
gcctctgctt tccagcgccg ggcaggaggg gtcctagttg cctcccatct gcagagcttc    480
ctggaggtgt cgtaccgcgt tctacgccac cttgcccagc cctga                    525
```

<210> SEQ ID NO 4
<211> LENGTH: 174
<212> TYPE: PRT
<213> ORGANISM: Homo sapiens

<400> SEQUENCE: 4

```
Thr Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
             20                  25                  30

Glu Lys Leu Cys Ala Thr Tyr Lys Leu Cys His Pro Glu Glu Leu Val
         35                  40                  45

Leu Leu Gly His Ser Leu Gly Ile Pro Trp Ala Pro Leu Ser Ser Cys
     50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
            115                 120                 125
```

-continued

Ala Leu Gln Pro Thr Gln Gly Ala Met Pro Ala Phe Ala Ser Ala Phe
130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 5
<211> LENGTH: 863
<212> TYPE: PRT
<213> ORGANISM: Homo sapiens

<400> SEQUENCE: 5

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
                20                  25                  30

Ala Pro Ile Val His Leu Gly Asp Pro Ile Thr Ala Ser Cys Ile Ile
            35                  40                  45

Lys Gln Asn Cys Ser His Leu Asp Pro Glu Pro Gln Ile Leu Trp Arg
50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

-continued

```
Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
            355                 360                 365

Gln Gly Tyr Val Val Ser Trp Arg Pro Ser Gly Gln Ala Gly Ala Ile
            370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                    405                 410                 415

Ser Arg Pro Thr Pro Val Val Phe Ser Glu Ser Arg Gly Pro Ala Leu
            420                 425                 430

Thr Arg Leu His Ala Met Ala Arg Asp Pro His Ser Leu Trp Val Gly
            435                 440                 445

Trp Glu Pro Pro Asn Pro Trp Pro Gln Gly Tyr Val Ile Glu Trp Gly
            450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                    485                 490                 495

Phe Gln Leu Tyr Glu Ile Ile Val Thr Pro Leu Tyr Gln Asp Thr Met
            500                 505                 510

Gly Pro Ser Gln His Val Tyr Ala Tyr Ser Gln Glu Met Ala Pro Ser
            515                 520                 525

His Ala Pro Glu Leu His Leu Lys His Ile Gly Lys Thr Trp Ala Gln
            530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                    565                 570                 575

Ile Leu Asn Ala Ser Ser Arg Gly Phe Val Leu His Gly Leu Glu Pro
            580                 585                 590

Ala Ser Leu Tyr His Ile His Leu Met Ala Ala Ser Gln Ala Gly Ala
            595                 600                 605

Thr Asn Ser Thr Val Leu Thr Leu Met Thr Leu Thr Pro Glu Gly Ser
            610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                    645                 650                 655

Pro Leu Trp Pro Ser Val Pro Asp Pro Ala His Ser Ser Leu Gly Ser
            660                 665                 670

Trp Val Pro Thr Ile Met Glu Glu Leu Pro Gly Pro Arg Gln Gly Gln
            675                 680                 685

Trp Leu Gly Gln Thr Ser Glu Met Ser Arg Ala Leu Thr Pro His Pro
            690                 695                 700

Cys Val Gln Asp Ala Phe Gln Leu Pro Gly Leu Gly Thr Pro Pro Ile
705                 710                 715                 720

Thr Lys Leu Thr Val Leu Glu Glu Asp Glu Lys Lys Pro Val Pro Trp
                    725                 730                 735

Glu Ser His Asn Ser Ser Glu Thr Cys Gly Leu Pro Thr Leu Val Gln
            740                 745                 750

Thr Tyr Val Leu Gln Gly Asp Pro Arg Ala Val Ser Thr Gln Pro Gln
            755                 760                 765
```

```
Ser Gln Ser Gly Thr Ser Asp Gln Val Leu Tyr Gly Gln Leu Leu Gly
    770                 775                 780
Ser Pro Thr Ser Pro Gly Pro Gly His Tyr Leu Arg Cys Asp Ser Thr
785                 790                 795                 800
Gln Pro Leu Leu Ala Gly Leu Thr Pro Ser Pro Lys Ser Tyr Glu Asn
                805                 810                 815
Leu Trp Phe Gln Ala Ser Pro Leu Gly Thr Leu Val Thr Pro Ala Pro
            820                 825                 830
Ser Gln Glu Asp Asp Cys Val Phe Gly Pro Leu Leu Asn Phe Pro Leu
        835                 840                 845
Leu Gln Gly Ile Arg Val His Gly Met Glu Ala Leu Gly Ser Phe
    850                 855                 860

<210> SEQ ID NO 6
<211> LENGTH: 3024
<212> TYPE: DNA
<213> ORGANISM: Homo sapiens

<400> SEQUENCE: 6
gaagctggac tgcagctggt ttcaggaact tctcttgacg agaagagaga ccaaggaggc    60
caagcagggg ctgggccaga ggtgccaaca tggggaaact gaggctcggc tcggaaaggt   120
gaagtaactt gtccaagatc acaaagctgg tgaacatcaa gttggtgcta tgcaaggct    180 gggaaactgc agcctgactt gggctgccct gatcatcctg ctgctccccg aagtctgga    240 ggagtgcggg cacatcagtg tctcagcccc atcgtccac ctgggggatc ccatcacagc   300
ctcctgcatc atcaagcaga actgcagcca tctggacccg agccacaga ttctgtggag   360 actgggagca gagcttcagc ccggggggcag gcagcagcgt ctgtctgatg ggacccagga   420
atctatcatc accctgcccc acctcaacca cactcaggcc tttctctcct gctgcctgaa   480
ctggggcaac agcctgcaga tcctggacca ggttgagctg cgcgcaggct accctccagc   540 catacccac aacctctcct gcctcatgaa cctcacaacc agcagcctca tctgccagtg   600
ggagccagga cctgagaccc acctaccac agcttcact ctgaagagtt tcaagagccg   660
gggcaactgt cagacccaag gggactccat cctggactgc gtgcccaagg acgggcagag   720
ccactgctgc atcccacgca aacacctgct gttgtaccag aatatgggca tctgggtgca   780
ggcagagaat gcgctgggga ccagcatgtc cccacaactg tgtcttgatc ccatggatgt   840
tgtgaaactg gagccccca tgctgcggac catggacccc agccctgaag cggcccctcc   900
ccaggcaggc tgcctacagc tgtgctggga gccatggcag ccaggcctgc acataaatca   960
gaagtgtgag ctgcgccaca gccgcagcg tggagaagcc agctgggcac tggtgggccc  1020
cctccccttg gaggcccttc agtatgagct ctgcgggctc ctcccagcca cggcctacac  1080
cctgcagata cgctgcatcc gctggcccct gcctggccac tggagcgact ggagccccag  1140
cctggagctg agaactaccg aacgggcccc cactgtcaga ctggacacat ggtggcggca  1200
gaggcagctg gacccaggag cagtgcagct gttctggaag ccagtgcccc tggaggaaga  1260
cagcggacgg atccaaggtt atgtggtttc ttggagaccc tcaggccagg ctggggccat  1320 cctgccctc tgcaacacca cagagctcag ctgcaccttc cacctgcctt cagaagccca  1380
ggaggtggcc cttgtggcct ataactcagc cgggacctct cgccccaccc cggtggtctt  1440
ctcagaaagc agaggcccag ctctgaccag actccatgcc atggcccgag accctcacag  1500
cctctgggta ggctgggagc cccccaatcc atggcctcag ggctatgtga ttgagtgggg  1560 cctgggccc cccagcgcga gcaatagcaa caagacctgg aggatggaac agaatgggag  1620
```

```
agccacgggg tttctgctga aggagaacat caggcccttt cagctctatg agatcatcgt    1680
gactcccttg taccaggaca ccatgggacc ctcccagcat gtctatgcct actctcaaga    1740
aatggctccc tcccatgccc cagagctgca tctaaagcac attggcaaga cctgggcaca    1800
gctggagtgg gtgcctgagc ccctgagct ggggaagagc cccttaccc actacaccat     1860 cttctggacc aacgctcaga accagtcctt ctccgccatc ctgaatgcct ctcccgtgg    1920 cttTgtcctc catggcctgg agcccgccag tctgtatcac atccacctca tggctgccag    1980
ccaggctggg gccaccaaca gtacagtcct caccctgatg accttgaccc cagaggggtc    2040
ggagctacac atcatcctgg gcctgttcgg cctcctgctg ttgctcacct gcctctgtgg    2100
aactgcctgg ctctgttgca gccccaacag gaagaatccc ctctggccaa gtgtcccaga    2160
cccagctcac agcagcctgg gctcctgggt gcccacaatc atggaggagc tgcccggacc    2220
cagacaggga cagtggctgg ggcagacatc tgaaatgagc cgtgctctca ccccacatcc    2280
ttgtgtgcag gatgccttcc agctgcccgg ccttggcacg ccacccatca ccaagctcac    2340
agtgctggag gaggatgaaa agaagccggt gccctgggag tcccataaca gctcagagac    2400
ctgtggcctc cccactctgg tccagaccta tgtgctccag ggggacccaa gagcagtttc    2460
cacccagccc caatcccagt ctggcaccag cgatcaggtc ctttatgggc agctgctggg    2520
cagccccaca agcccagggc cagggcacta tctccgctgt gactccactc agcccctctt    2580
ggcgggcctc acccccagcc ccaagtccta tgagaacctc tggttccagg ccagccccTT    2640
ggggaccctg gtaaccccag ccccaagcca ggaggacgac tgtgtctttg gccactgct    2700 caacttcccc ctcctgcagg ggatccgggt ccatgggatg gaggcgctgg ggagcttcta    2760
gggcttcctg gggttccctt cttgggcctg cctcttaaag gcctgagcta gctggagaag    2820
aggggagggt ccataagccc atgactaaaa actaccccag cccaggctct caccatctcc    2880
agtcaccagc atctccctct cctcccaatc tccataggct gggcctccca ggcgatctgc    2940
atactttaag gaccagatca tgctccatcc agccccaccc aatggccttt tgtgcttgtt    3000
tcctataact tcagtattgt aaac                                           3024
```

<210> SEQ ID NO 7
<211> LENGTH: 2520
<212> TYPE: DNA
<213> ORGANISM: Homo sapiens

<400> SEQUENCE: 7

```
gagtgcgggc acatcagtgt ctcagccccc atcgtccacc tggggatcc catcacagcc      60 tcctgcatca tcaagcagaa ctgcagccat ctggacccgg agccacagat tctgtggaga    120
ctgggagcag agcttcagcc cggggcagg cagcagcgtc tgtctgatgg gacccaggaa    180
tctatcatca ccctgcccca cctcaaccac actcaggcct ttctctcctg ctgcctgaac    240
tggggcaaca gcctgcagat cctggaccag gttgagctgc gcgcaggcta ccctccagcc    300
atacccacac acctctcctg cctcatgaac ctcacaacca gcagcctcat ctgccagtgg    360
gagccaggac ctgagaccca cctacccacc agcttcactc tgaagagttt caagagccgg    420
ggcaactgtc agacccaagg ggactccatc ctggactgcg tgcccaagga cgggcagagc    480
cactgctgca tccacgcaa acacctgctg ttgtaccaga atatgggcat ctgggtgcag    540
gcagagaatg cgctggggac cagcatgtcc ccacaactgt gtcttgatcc catggatgtt    600
gtgaaactgg agccccccat gctgcggacc atggaccca gccctgaagc ggcccctccc    660
caggcaggct gcctacagct gtgctgggag ccatggcagc caggcctgca cataaatcag    720
```

```
aagtgtgagc tgcgccacaa gccgcagcgt ggagaagcca gctgggcact ggtgggcccc    780 ctcccttgg aggcccttca gtatgagctc tgcgggctcc tcccagccac ggcctacacc     840
ctgcagatac gctgcatccg ctggcccctg cctggccact ggagcgactg gagccccagc    900
ctggagctga gaactaccga acgggccccc actgtcagac tggacacatg gtggcggcag    960
aggcagctgg accccaggac agtgcagctg ttctggaagc cagtgcccct ggaggaagac   1020
agcggacgga tccaaggtta tgtggtttct tggagaccct caggccaggc tggggccatc   1080
ctgcccctct gcaacaccac agagctcagc tgcaccttcc acctgccttc agaagcccag   1140
gaggtggccc ttgtggccta aactcagcc gggacctctc gccccacccc ggtggtcttc    1200
tcagaaagca gaggcccagc tctgaccaga ctccatgcca tggcccgaga ccctcacagc   1260
ctctgggtag gctgggagcc ccccaatcca tggcctcagg gctatgtgat tgagtggggc   1320 ctgggcccc ccagcgcgag caatagcaac aagacctgga ggatggaaca gaatgggaga    1380
gccacggggt ttctgctgaa ggagaacatc aggccctttc agctctatga gatcatcgtg   1440
actcccttgt accaggacac catgggaccc tcccagcatg tctatgccta ctctcaagaa   1500
atggctccct cccatgcccc agagctgcat ctaaagcaca ttggcaagac ctgggcacag   1560
ctggagtggg tgcctgagcc ccctgagctg gggaagagcc cccttaccca ctacaccatc   1620
ttctggacca acgctcagaa ccagtccttc tccgccatcc tgaatgcctc ctcccgtggc   1680
tttgtcctcc atggcctgga gcccgccagt ctgtatcaca tccacctcat ggctgccagc   1740
caggctgggg ccaccaacag tacagtcctc accctgatga ccttgacccc agaggggtcg   1800
gagctacaca tcatcctggg cctgttcggc ctcctgctgt tgctcacctg cctctgtgga   1860
actgcctggc tctgttgcag ccccaacagg aagaatcccc tctggccaag tgtcccagac   1920
ccagctcaca gcagcctggg ctcctgggtg cccacaatca tggaggagct gcccggaccc   1980
agacagggac agtggctggg gcagacatct gaaatgagcc gtgctctcac cccacatcct   2040
tgtgtgcagg atgccttcca gctgcccggc cttggcacgc cacccatcac caagctcaca   2100
gtgctggagg aggatgaaaa gaagccggtg ccctgggagt cccataacag ctcagagacc   2160
tgtggcctcc ccactctggt ccagacctat gtgctccagg gggacccaag agcagtttcc   2220
acccagcccc aatcccagtc tggcaccagc gatcaggtcc tttatgggca gctgctgggc   2280
agccccacaa gcccagggcc agggcactat ctccgctgtg actccactca gcccctcttg   2340 gcggcctca cccccagccc caagtcctat gagaacctct ggttccaggc cagcccttg    2400 gggaccctgg taacccccagc cccaagccag gaggacgact gtgtctttgg ccactgctc    2460 aacttccccc tcctgcaggg gatccgggtc catgggatgg aggcgctggg gagcttctag   2520
```

<210> SEQ ID NO 8
<211> LENGTH: 839
<212> TYPE: PRT
<213> ORGANISM: Homo sapiens

<400> SEQUENCE: 8

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Pro Glu Pro Gln Ile Leu Trp Arg Leu Gly Ala Glu Leu Gln Pro Gly
        35                  40                  45

Gly Arg Gln Gln Arg Leu Ser Asp Gly Thr Gln Glu Ser Ile Ile Thr
    50                  55                  60

```
Leu Pro His Leu Asn His Thr Gln Ala Phe Leu Ser Cys Cys Leu Asn
 65                  70                  75                  80

Trp Gly Asn Ser Leu Gln Ile Leu Asp Gln Val Glu Leu Arg Ala Gly
                 85                  90                  95

Tyr Pro Pro Ala Ile Pro His Asn Leu Ser Cys Leu Met Asn Leu Thr
            100                 105                 110

Thr Ser Ser Leu Ile Cys Gln Trp Glu Pro Gly Pro Glu Thr His Leu
        115                 120                 125

Pro Thr Ser Phe Thr Leu Lys Ser Phe Lys Ser Arg Gly Asn Cys Gln
    130                 135                 140

Thr Gln Gly Asp Ser Ile Leu Asp Cys Val Pro Lys Asp Gly Gln Ser
145                 150                 155                 160

His Cys Cys Ile Pro Arg Lys His Leu Leu Tyr Gln Asn Met Gly
                165                 170                 175

Ile Trp Val Gln Ala Glu Asn Ala Leu Gly Thr Ser Met Ser Pro Gln
                180                 185                 190

Leu Cys Leu Asp Pro Met Asp Val Val Lys Leu Glu Pro Pro Met Leu
        195                 200                 205

Arg Thr Met Asp Pro Ser Pro Glu Ala Ala Pro Pro Gln Ala Gly Cys
    210                 215                 220

Leu Gln Leu Cys Trp Glu Pro Trp Gln Pro Gly Leu His Ile Asn Gln
225                 230                 235                 240

Lys Cys Glu Leu Arg His Lys Pro Gln Arg Gly Glu Ala Ser Trp Ala
                245                 250                 255

Leu Val Gly Pro Leu Pro Leu Glu Ala Leu Gln Tyr Glu Leu Cys Gly
                260                 265                 270

Leu Leu Pro Ala Thr Ala Tyr Thr Leu Gln Ile Arg Cys Ile Arg Trp
        275                 280                 285

Pro Leu Pro Gly His Trp Ser Asp Trp Ser Pro Ser Leu Glu Leu Arg
    290                 295                 300

Thr Thr Glu Arg Ala Pro Thr Val Arg Leu Asp Thr Trp Trp Arg Gln
305                 310                 315                 320

Arg Gln Leu Asp Pro Arg Thr Val Gln Leu Phe Trp Lys Pro Val Pro
                325                 330                 335

Leu Glu Glu Asp Ser Gly Arg Ile Gln Gly Tyr Val Val Ser Trp Arg
                340                 345                 350

Pro Ser Gly Gln Ala Gly Ala Ile Leu Pro Leu Cys Asn Thr Thr Glu
        355                 360                 365

Leu Ser Cys Thr Phe His Leu Pro Ser Glu Ala Gln Glu Val Ala Leu
    370                 375                 380

Val Ala Tyr Asn Ser Ala Gly Thr Ser Arg Pro Thr Pro Val Val Phe
385                 390                 395                 400

Ser Glu Ser Arg Gly Pro Ala Leu Thr Arg Leu His Ala Met Ala Arg
                405                 410                 415

Asp Pro His Ser Leu Trp Val Gly Trp Glu Pro Pro Asn Pro Trp Pro
                420                 425                 430

Gln Gly Tyr Val Ile Glu Trp Gly Leu Gly Pro Pro Ser Ala Ser Asn
        435                 440                 445

Ser Asn Lys Thr Trp Arg Met Glu Gln Asn Gly Arg Ala Thr Gly Phe
    450                 455                 460

Leu Leu Lys Glu Asn Ile Arg Pro Phe Gln Leu Tyr Glu Ile Ile Val
465                 470                 475                 480

Thr Pro Leu Tyr Gln Asp Thr Met Gly Pro Ser Gln His Val Tyr Ala
```

```
                485                 490                 495
Tyr Ser Gln Glu Met Ala Pro Ser His Ala Pro Glu Leu His Leu Lys
            500                 505                 510

His Ile Gly Lys Thr Trp Ala Gln Leu Glu Trp Val Pro Glu Pro Pro
            515                 520                 525

Glu Leu Gly Lys Ser Pro Leu Thr His Tyr Thr Ile Phe Trp Thr Asn
            530                 535                 540

Ala Gln Asn Gln Ser Phe Ser Ala Ile Leu Asn Ala Ser Ser Arg Gly
545                 550                 555                 560

Phe Val Leu His Gly Leu Glu Pro Ala Ser Leu Tyr His Ile His Leu
                565                 570                 575

Met Ala Ala Ser Gln Ala Gly Ala Thr Asn Ser Thr Val Leu Thr Leu
            580                 585                 590

Met Thr Leu Thr Pro Glu Gly Ser Glu Leu His Ile Ile Leu Gly Leu
            595                 600                 605

Phe Gly Leu Leu Leu Leu Leu Thr Cys Leu Cys Gly Thr Ala Trp Leu
            610                 615                 620

Cys Cys Ser Pro Asn Arg Lys Asn Pro Leu Trp Pro Ser Val Pro Asp
625                 630                 635                 640

Pro Ala His Ser Ser Leu Gly Ser Trp Val Pro Thr Ile Met Glu Glu
                645                 650                 655

Leu Pro Gly Pro Arg Gln Gly Gln Trp Leu Gly Gln Thr Ser Glu Met
            660                 665                 670

Ser Arg Ala Leu Thr Pro His Pro Cys Val Gln Asp Ala Phe Gln Leu
            675                 680                 685

Pro Gly Leu Gly Thr Pro Ile Thr Lys Leu Thr Val Leu Glu Glu
            690                 695                 700

Asp Glu Lys Lys Pro Val Pro Trp Glu Ser His Asn Ser Ser Glu Thr
705                 710                 715                 720

Cys Gly Leu Pro Thr Leu Val Gln Thr Tyr Val Leu Gln Gly Asp Pro
                725                 730                 735

Arg Ala Val Ser Thr Gln Pro Gly Ser Gln Ser Gly Thr Ser Asp Gln
            740                 745                 750

Val Leu Tyr Gly Gln Leu Leu Gly Ser Pro Thr Ser Pro Gly Pro Gly
            755                 760                 765

His Tyr Leu Arg Cys Asp Ser Thr Gln Pro Leu Leu Ala Gly Leu Thr
            770                 775                 780

Pro Ser Pro Lys Ser Tyr Glu Asn Leu Trp Phe Gln Ala Ser Pro Leu
785                 790                 795                 800

Gly Thr Leu Val Thr Pro Ala Pro Ser Gln Glu Asp Asp Cys Val Phe
                805                 810                 815

Gly Pro Leu Leu Asn Phe Pro Leu Leu Gln Gly Ile Arg Val His Gly
            820                 825                 830

Met Glu Ala Leu Gly Ser Phe
            835
```

METHOD OF TREATING PULMONARY DISEASE BY ADMINISTERING AN ANTIBODY TO G-CSF RECEPTOR

RELATED APPLICATIONS

This application is a U.S. National Phase of International Application No. PCT/AU2007/001127, filed Aug. 10, 2007 and published in English on Feb. 14, 2008.

FIELD

The present invention relates generally to a method for treating or preventing or otherwise ameliorating the effects of pulmonary diseases characterized by or associated with infiltration of neutrophils and complications arising therefrom. The present invention further provides agents and pharmaceutical compositions comprising agents which inhibit the activity of G-CSF or its receptor, interfere with G-CSF signaling and/or which down-regulate expression of G-CSF or its receptor.

BACKGROUND

Bibliographic details of references provided in the subject specification are listed at the end of the specification.

Reference to any prior art is not, and should not be taken as an acknowledgment or any form of suggestion that this prior art forms part of the common general knowledge in any country.

Chronic obstructive pulmonary disease (COPD) is a major global health burden and will become the third largest cause of death in the world by 2020 (Lopez and Murray, Nat Med 4(11):1241-1243, 1998). An exaggerated inflammatory response to inhaled irritants, in particular cigarette smoke, is the likely cause of a progressive airflow limitation. This inflammation, where macrophages and neutrophils are prominent, leads to oxidative stress, emphysema, small airway fibrosis and mucus hypersecretion. However, COPD responds poorly to current anti-inflammatory treatments including potent glucocorticosteroids which produce little or no benefit. COPD lungs may also become colonized with Gram negative and Gram positive bacteria which hasten lung function decline and, along with viruses and inhaled pollutants, are major triggers of recurrent debilitating exacerbations. COPD patients suffer recurrent acute exacerbations (AECOPD) caused by both viruses and bacteria.

Histological and bronchial biopsy studies show that patients with COPD have an increased number of neutrophils (Di Stefano et al, Am J Respir Crit Care Med 158(4):1277-1285, 1998; Retamales et al, Am J Respir Crit Care Med 164:469-473, 2001). In addition, BALF and sputum of COPD patients have a marked increase in neutrophils (Pesci et al, Eur Respir J 12(2):380-386, 1998; Keatings et al, Am J Respir Crit Care Med 153(2):530-534, 1996). Neutrophil numbers in bronchial biopsies and induced sputum are correlated with COPD disease severity (Di Stefano et al, 1998 supra, Keatings et al, 1996 supra) and with the rate of decline in lung function (Stanescu et al, Thorax 51(3):267-271, 1996). Neutrophils secrete serine proteases, including neutrophil elastase, cathepsin G and protease-3, as well as MMP-8 and MMP-9, which contribute to alveolar destruction and produce emphysema in laboratory animals (Stockely, Am J Respir Crit Care Med 160(5 Pt 2):S49-52, 1999; Barnes et al, Eur Respir J 22:672-688, 2003). Neutrophils migrate into the respiratory tract under the direction of neutrophil chemotactic factors, which include IL-8 (Barnes et al, supra 2003). Serine proteases are potent stimulants of mucus hypersecretion and may have an important role in the mucus hypersecretion seen in chronic bronchitis (Sommerhoff et al, J Clin Invest 85(3): 682-289, 1990).

One cytokine involved in inflammatory reactions is granulocyte colony-stimulating factor (G-CSF) which is encoded by the CSF-3 gene. G-CSF is a hemopoietic growth factor that regulates the production of granulocytes (Nicola et al, Nature 314:625, 1985; Metcalf, International Journal of Cancer 25:225, 1980; Nicola et al, Journal of Biological Chemistry 258:9017, 1983). G-CSF mediates its effects through interaction with the G-CSF receptor (G-CSFR, encoded by the CSFR-3 gene), a member of the type I cytokine receptor superfamily (Demetri et al, Blood 78:2791-2808, 1991). Major biological actions of G-CSF in humans and mice, include increasing the production and release of neutrophils from the bone marrow (Souza et al, Science 232:61, 1986; Lord et al, Proc. Natl. Acad. Sci. USA 86:9499-9503, 1989), mobilizing hemopoietic progenitor cells from the marrow into the peripheral blood (Bungart et al, British Journal of Haematology 22:1156, 1990; de Haan et al, Blood 86:2986-2992, 1995; Roberts et al, Blood 89:2736-2744, 1997) and modulating the differentiation and effector functions of mature neutrophils (Yong et al, European Journal of Haematology 49:251-259, 1992; Colotta et al, Blood 80:2012-2020, 1992; Rex et al, Transfusion 35:605-611, 1995; Gericke et al, Journal of Leukocyte Biology 57:455-461, 1995; Xu et al, British Journal of Haematology 93:558-568, 1996; Yong, British Journal of Haematology 94:40-47, 1996; Jacob et al, Blood 92:353-361, 1998). G-CSF is used to treat neutropenia, as well as mobilization of haemopoietic stem cells (HSC) for autologous and allogenic stem cell transplantation (Welte et al, Blood 88:1907-1929, 1996).

There is an urgent and immediate need to develop new treatments for inflammatory conditions such as COPD, its exacerbated forms such as AECOPD and other pulmonary diseases characterized by or associated with infiltration of neutrophils.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2); etc. A summary of the sequence identifiers is provided in Table 1. A sequence listing is provided after the claims.

The present invention relates generally to the use of antagonists of activity of G-CSF, its receptor and/or which inhibit expression of genes encoding G-CSF or its receptor in the treatment of pulmonary diseases or conditions characterized by or associated with infiltration of neutrophils. In particular, the present invention contemplates the treatment of chronic immune-mediated inflammatory pulmonary disease (COPD), exacerbated forms thereof such as acute exacerbated COPD (AECOPD) and complications arising therefrom or manifestations thereof such as chronic bronchitis, oxidative stress, emphysema, mucus hypersecretion, arrhythmias, cor pulmonale pneumonia and lung cancer.

The present invention is predicated in part on the elucidation of the role of G-CSF in relation to COPD or its exacerbated forms (e.g. AECOPD) or complications therefrom or manifestations thereof. In accordance with the present invention, therefore, inhibiting the activity of G-CSF or G-CSFR systemically or locally and/or down-regulating expression of a gene encoding a G-CSF or G-CSFR is proposed to be useful in the treatment of pulmonary conditions characterized by or associated with infiltration of neutrophils.

Reference to "G-CSF" or its full name "granulocyte-colony stimulating factor" includes homologs and derivatives of G-CSF. A "homolog" or "derivative" includes polymorphic variants of G-CSF.

Reference to "G-CSFR" or its full name "granulocyte-colony stimulating factor" includes homologs and derivatives of G-CSFR. A "homolog" or "derivative" includes polymorphic variants of G-CSF.

Accordingly, one aspect of the present invention contemplates a method for the treatment of a pulmonary condition characterized by or associated with infiltration of neutrophils in a subject, said method comprising administering to said subject an amount of an agent effective to inhibit the activity of G-CSF or G-CSFR or inhibit expression of the gene encoding G-CSF or G-CSFR.

In a particular embodiment, a method is provided for treating a pulmonary disease associated with neutrophil infiltration in a subject, said method comprising administering to said subject a G-CSF or G-CSFR inhibiting agent selected from the group consisting of:
  a. an antibody specific for G-CSF;
  b. an antibody specific for G-CSFR;
  c. a soluble G-CSFR or a G-CSF-binding portion thereof;
  d. a sense or antisense molecule 20 to 30 nucleobases in length targeted to a nucleic acid molecule encoding G-CSF, wherein the nucleotide sequence comprises the sequence set forth in SEQ ID NO:3; and
  e. a sense or antisense molecule 20 to 30 nucleobases in length targeted to a nucleic acid molecule encoding a G-CSFR, wherein the nucleotide sequence comprises the sequence set forth in SEQ ID NO:7.

Generally, the agent is administered for a time and under conditions sufficient to ameliorate the symptoms of the pulmonary condition.

In a particular embodiment, the pulmonary condition is COPD or one or more complications arising therefrom or a manifestation thereof.

More particularly, the present invention is directed to a method for the treatment of COPD or an exacerbated form thereof or a related condition or a complication arising from same or a manifestation thereof in a subject said method comprising administering to said subject an amount of an agent effective to inhibit the activity of G-CSF or G-CSFR or inhibit expression of the gene encoding G-CSF or G-CSFR.

The administration may be systemic or local. Systemic administration is particularly useful. Reference to "systemic administration" includes intra-articular, intravenous, intraperitoneal, and subcutaneous injection, infusion, as well as administration via oral, rectal and nasal routes, or via inhalation. Administration by subcutaneous injection or via inhalation is particularly preferred.

The agents may be proteinaceous, non-proteinaceous (e.g. chemical entities) or nucleic acid molecules.

Proteinaceous and non-proteinaceous molecules include peptides, polypeptides and proteins, small, intermediate or large chemical molecules as well as molecules identified from natural product screening or the screening of chemical libraries. Natural product screening includes the screening of extracts or samples from plants, microorganisms, soil river beds, coral, aquatic environments and extraterrestrial environments for molecules or groups of molecules which have an affect on G-CSF activity or the level of G-CSF gene expression. These molecules may also affect G-CSF/G-CSFR interaction.

The present invention further contemplates combination therapy such as targeting G-CSF and/or G-CSFR and one or more other inflammatory targets.

Accordingly, another aspect of the present invention relates to a method for the treatment of a pulmonary condition characterized by or associated with infiltration of neutrophils such as but not limited to COPD or an exacerbated form thereof such as AECOPD, a related condition or a complication arising therefrom or a manifestation thereof in a subject, said method comprising administering an agent which inhibits the activity of G-CSF or G-CSFR or inhibits the expression of the gene encoding G-CSF or G-CSFR and at least one other therapeutic agent such as an anti-inflammatory, a bronchodilator or an antibiotic.

One preferred agent is an antibody which inhibits the activity of G-CSF or G-CSFR. Other useful agents include small molecule inhibitors, soluble G-CSF receptors and nucleic acid molecules which inhibit G-CSF or G-CSFR gene expression. The antibody may be mono-specific or multi-specific including bi-specific.

Hence, in a particularly preferred embodiment, the present invention contemplates a method for the treatment of COPD or an exacerbated form thereof or a related condition or a complication arising from same or a manifestation thereof in a subject said method comprising administering to said subject an amount of an antibody effective to inhibit the activity of G-CSF or G-CSFR.

Whilst sense or antisense molecules directed to the G-CSF gene or mRNA or G-CSFR gene or mRNA are provided, sense or antisense molecules are also provided against any portion of the coding or non-coding regions including leader sequence and selected introns or extons of the G-CSF or G-CSFR gene or mRNA. Hence, sense and antisense molecules of 20 to 30 nucleotide basis in length are contemplated to one or more of SEQ ID NOs:2, 3, 6 or 7.

The preferred subjects are mammals and in particular humans.

The present invention extends to the use of pharmaceutical compositions comprising antagonists of G-CSF or G-CSFR activity or gene expression. One particularly useful composition comprises an anti-G-CSF antibody or an anti-G-CSFR antibody.

The present invention further contemplates the use of an antibody to G-CSF or G-CSFR in the manufacture of a medicament for the treatment of COPD or an exacerbated form thereof or a related condition or a complication arising from same or a manifestation thereof in a subject.

Another aspect provides for the use of an agent which inhibits the activity of G-CSF or G-CSFR or which inhibits expression of a gene encoding G-CSF or G-CSFR in the manufacture of a medicament for treating a pulmonary disease associated with neutrophil infiltration in a subject, wherein said agent is selected from the group consisting of:
  a. an antibody specific for G-CSF;
  b. an antibody specific for G-CSFR;
  c. a soluble G-CSFR or a G-CSF-binding portion thereof;
  d. a sense or antisense molecule 20 to 30 nucleobases in length targeted to a nucleic acid molecule encoding G-CSF, wherein the nucleotide sequence comprises the sequence set forth in SEQ ID NO:3; and
  e. a sense or antisense molecule 20 to 30 nucleobases in length targeted to a nucleic acid molecule encoding a G-CSFR, wherein the nucleotide sequence comprises the sequence set forth in SEQ ID NO:7.

A summary of sequence identifiers used throughout the subject specification is provided in Table 1.

TABLE 1

Summary of sequence identifiers

| SEQUENCE ID NO: | DESCRIPTION |
|---|---|
| 1 | Human G-CSF amino acid sequence including the leader sequence |
| 2 | Human G-CSF coding and non-coding nucleotide sequence |
| 3 | Human G-CSF nucleotide sequence encoding mature protein |
| 4 | Human G-CSF mature protein amino acid sequence |
| 5 | Human G-CSFR3 amino acid sequence including the leader sequence |
| 6 | Human G-CSF3R coding and non-coding nucleotide sequence |
| 7 | Human G-CSF3R nucleotide sequence encoding mature protein |
| 8 | Human G-CSF3R mature protein amino acid sequence |

DETAILED DESCRIPTION

Figure 1:
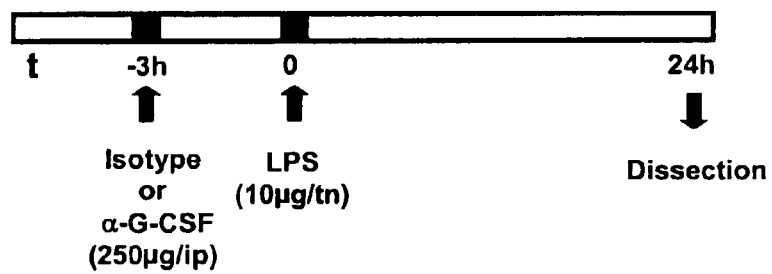
FIG. 1 is a graphical representation showing mice treated with either isotype control or 250 µg/dose ip of anti-G-CSF antibody (also referred to as αG-CSF antibody or anti-GCSF) at t=−3 hour, exposed to one dose of LPS at t=0, and then dissected 24 hours later.

Before describing the present invention in detail, it is to be understood that unless otherwise indicated, the subject invention is not limited to specific formulations of components, manufacturing methods, dosage or diagnostic regimes, or the like. It is also to be understood that the terminology used herein is for the purpose of describing particular embodiments only and is not intended to be limiting.

The singular forms "a", "an" and "the" include plural aspects unless the context clearly dictates otherwise. Thus, for example, reference to "a cytokine" includes a single cytokine as well as two or more cytokines; reference to "an antibody" includes a single antibody, as well as two or more antibodies; reference to "the invention" includes a single invention or multiple invention; and so forth.

In describing and claiming the present invention, the following terminology is used in accordance with the definitions set forth below.

The terms "agent", "compound", and "active" may be used interchangeably herein to refer to a substance that induces a desired pharmacological and/or physiological effect. The terms also encompass pharmaceutically acceptable and pharmacologically active forms thereof, including salts. The desired effect is the inhibition of G-CSF activity or signaling or inhibition of expression of a gene encoding G-CSF or its receptor.

Combination therapy involving the use of a G-CSF or G-CSFR antagonist together with another therapeutic agent such as an anti-inflammatory, a bronchodilator and/or an antibiotic is also contemplated by the present invention.

One preferred agent is an antibody specific for a G-CSF or G-CSFR.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab')₂ fragments; and antibody-derived polypeptides produced using recombinant methods such as single chain antibodies. The terms "antibody" and "antibodies" as used herein also refer to human antibodies produced for example in transgenic animals or through phage display, as well as chimeric antibodies, humanized antibodies or primatized antibodies. The selection of fragment or modified forms of the antibodies may also involve any effect the fragments or modified forms have on their half-lives. For example, it may in certain circumstances be advantages for an antibody to have a short half-life to avoid global affects of anti-G-CSF treatment, such as neutropenia. Alternatively, where exacerbations are common or likely, an antibody with a longer half-life may be advantageous. A "half-life" for an antibody is considered herein to be short if it is within 2 days or less. A longer half-life for an antibody would be any half-life in excess of 2 days and more preferably may be greater than 7 days.

The term "monoclonal antibody" is used herein to refer to an antibody obtained from a population of substantially homogeneous antibodies. That is, the individual antibodies comprising the population are identical except for naturally occurring mutations that may be present in minor amounts. The modifier "monoclonal" as used herein therefore indicates the character of the antibody as being obtained from a substantially homogeneous population of antibodies, and is not used to indicate that the antibody was produced by a particular method. For example, monoclonal antibodies in accordance with the present invention may be made by the hybridoma method described by Kohler and Milstein, *Nature* 256:

495-499, 1975, or may be made by recombinant DNA methods (such as described in U.S. Pat. No. 4,816,567). Monoclonal antibodies may also be isolated from phage antibody libraries using the techniques described in Clackson et al, *Nature* 352:624-628, 1991 or Marks et al, *J. Mol. Biol.* 222:581-597, 1991.

The terms "effective amount" and "therapeutically effective amount" as used herein mean a sufficient amount of an agent which provides the desired therapeutic or physiological effect or outcome, inhibiting the activity of G-CSF or G-CSFR or which inhibits expression of a gene encoding G-CSF or G-CSFR. In addition, the effect may be an amelioration of the symptoms of the pulmonary condition such as COPD or an exacerbated form thereof (e.g. AECOPD), related conditions and/or complications arising from same or manifestations thereof. Undesirable effects, e.g. side effects, may sometimes manifest along with the desired therapeutic effect; hence, a practitioner balances the potential benefits against the potential risks in determining what is an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. For example, the ability of an αG-CSF antibody to ameliorate the effects of COPD or an exacerbated form thereof can be evaluated in an animal model system. One of ordinary skill in the art would be able to determine the required amounts based on such factors as the subject's size, the severity of the subject's symptoms, and the particular composition or route of administration selected.

Insofar as one embodiment of the present invention relates to the use of antibodies to G-CSF or its receptor, the effective amount include from about 10 µg/kg body weight to 20 mg/kg body weight of antibody such as 10, 20, 30, 40, 50, 60, 70, 80, 90, 100 µg/kg body weight, 100, 200, 300, 400, 500, 600, 700, 800, 900, 1000 µg/kg body weight or 2, 3, 4, 5, 6, 7, 8, 9, 10, 11, 12, 13, 14, 15, 16, 17, 18, 19 or 20 mg/kg body weight. Similar amounts are provided for single or combination therapy.

Reference to "a pulmonary condition or disease" includes any exaggerated or excessive or prolonged inflammatory response in the lungs or pulmonary system, which may be stimulated by a foreign object or irritant such as but not limited to smoke, dust, fumes, particles, bacteria, fungi, yeast or viruses. A range of complications and manifestations of the pulmonary condition are contemplated herein including exacerbated forms (e.g. AECOPD), oxidative stress, emphysema, bronchitis, mucus hypersecretion, cor pulmonale (right sided heart failure or enlargement of the heart and heart failure associated with chronic lung disease), arrhythmias, pneumonia and lung cancer. The complications and manifestations including acute respiratory distress syndrome and acute lung injury. The pulmonary condition may be chronic or acute or a stage inbetween. Recurring acute forms such as exacerbations of a chronic condition are also contemplated by the present invention.

The present invention is particularly directed to COPD and its exacerbated forms (e.g. AECOPD) and its related conditions and complications and manifestations thereof as outlined above.

A "pharmaceutically acceptable" carrier and/or diluent is a pharmaceutical vehicle comprised of a material that is not biologically or otherwise undesirable, i.e. the material may be administered to a subject along with the selected active agent without causing any or a substantial adverse reaction. Carriers may include any and all solvents, dispersion media, coatings, antibacterial and antifungal agents, agents used for adjusting tonicity, buffers, chelating agents, and absorption delaying agents and the like.

Similarly, a "pharmacologically acceptable" salt of a compound as provided herein is a salt, that is not biologically or otherwise undesirable.

The terms "treating" and "treatment" as used herein refer to therapeutic treatment and may include prophylactic or preventative measures. For example, treatment may result in a reduction in severity and/or the frequency of symptoms of the pulmonary disease, the elimination of symptoms and/or underlying cause of the inflammation, the prevention of the occurrence of symptoms of inflammation and/or their underlying cause and improvement or remediation or amelioration of damage following inflammation. Hence, the treatment may not result in a "cure" but rather an amelioration of symptoms. In addition, treatment may not commence until an exacerbated event occurs. In this context, the term "prophylactic" also applies to the prevention or treatment of a likelihood of an exacerbated event occurring.

The terms "treating" and "treatment" as used herein also refer to the reduction of one or more symptoms or characteristics associated with pulmonary diseases characterised by or associated with infiltration of neutrophils. Such symptoms or characteristics include increased neutrophil infiltration, increased neutrophils in BALF and sputum, declined lung function, increased levels of serine proteases, such as, but not limited to, neutrophil elastase, cathepsin G and protease-3, as well as MMD-8 and MMP-9.

Similarly, chimeric antibodies may include antibodies to G-CSF or G-CSFR comprising the heavy and light chain variable regions of rat or rabbit antibodies to G-CSF or G-CSFR and human heavy and light chain constant domains.

The terms "condition" and "disease" are used interchangeably throughout the subject specification.

A "subject" as used herein refers to an animal, preferably a mammal and more preferably a human who can benefit from the pharmaceutical compositions and methods of the present invention. There is no limitation on the type of animal that could benefit from the presently described pharmaceutical compositions and methods. A subject regardless of whether a human or non-human animal may be referred to as an individual, patient, animal, host or recipient as well as subject. The compounds and methods of the present invention have applications in human medicine and veterinary medicine.

Preferred mammals are humans and laboratory test animals. Examples of laboratory test animals include mice, rats, rabbits, guinea pigs, hamsters, cats and dogs.

One particularly useful agent of the present invention is an antibody to either G-CSF or G-CSFR that inhibits G-CSF signalling through the G-CSF receptor. Such antibodies to G-CSF may be referred to as anti-G-CSF antibodies or as αG-CSF, and antibodies to G-CSFR may be referred to as anti-G-CSFR antibodies or as αG-CSFR.

Although both polyclonal and monoclonal antibodies can be readily produced monoclonal antibodies are particularly preferred as they can be generated in large quantities, are highly specific and are directed against a single antigenic site. Furthermore, the monoclonal antibody preparations are homogeneous, making them ideal for generating antigen-binding fragments and other engineered antibody derivatives for therapeutic applications.

Although polyclonal antibodies are also relatively easily prepared, they are not as useful as monoclonal antibodies as polyclonal antibody preparations typically include different antibodies directed against different antigenic sites and thus are not as suitable for generating antigen-binding fragments and other engineered antibody derivatives for therapeutic applications.

The hybridoma method described above is used in animals, such as mice, to produce monoclonal antibodies. However, antibodies derived from animals are generally unsuitable for administration to humans as they may cause an immune response. As described below, such antibodies may be modified to become suitable for administration to humans or the desired non-human subject.

The αG-CSF antibodies, for example, may also be produced using recombinant methods (for example, in an *E. coli* expression system) well known in the art. In this approach, DNA encoding monoclonal antibodies, such as the murine monoclonal antibodies of the present invention, may be isolated from the hybridoma cell lines, sequenced using standard procedures and optionally manipulated using recombinant DNA technology. For example, the DNA may be fused to another DNA of interest, or altered (such as by mutagenesis or other conventional techniques) to add, delete, or substitute one or more nucleic acid residues. The DNA may be placed into vectors which are then transfected or transformed into appropriate host cells using methods well known in the art (such as described in U.S. Pat. Nos. 4,399,216; 4,912,040; 4,740,461 and 4,959,455). The DNA isolated from the hybridoma cell lines may also be modified to change the character of the antibody produced by its expression.

For example, chimeric forms of murine αG-CSF monoclonal antibodies may be produced by replacing the nucleotides encoding selected murine heavy and light chain constant domains with nucleotides encoding human heavy and light chain constant domains, such as is described in U.S. Pat. No. 4,816,567 and by Morrison et al, *Proc. Nat. Acad. Sci.* 81:6851, 1984. The chimeric antibodies may then be produced in an appropriate cell line, such as a murine myeloma cell line, that has been transfected with modified DNA.

Thus, among the antibodies contemplated by the present invention are chimeric αG-CSF antibodies that comprise the heavy and light chain variable regions of the murine CCG-CSF monoclonal antibody fused to non-murine heavy and light chain antibody constant domains. Preferably, the non-murine heavy and light chain constant domains are human heavy and light chain antibody constant domains. Similarly, chimeric antibodies may include antibodies to G-CSF or G-CSFR comprising the heavy and light chain variable regions of rat or rabbit antibodies to G-CSF or G-CSFR and human heavy and light chain constant domains.

The αG-CSF antibodies for use in the present invention also include humanized antibodies. In general, humanized antibodies are human antibodies (the recipient antibody) in which the complementarity determining (CDR) region residues have been replaced by CDR region residues from a non-human species (the donor antibody), such as from a mouse, rat, rabbit or non-human primate. In some cases, certain framework region (FR) residues of the human antibody may also be replaced by corresponding non-human residues, or the humanized antibodies may comprise residues which are not found in the recipient antibody or in the donor antibody. These modifications are made to enhance antibody performance and affinity. In general, the humanized antibody will comprise substantially all of at least one, and typically two, variable regions, in which all or substantially all of the CDR regions correspond to those of a non-human antibody, and all or substantially all of the FRs are those of a human antibody sequence. The humanized antibody may also optionally comprise at least a portion of an antibody constant region (Fc), typically that of a human antibody. (Jones et al, *Nature* 321:522-525, 1986; Reichmann et al, *Nature* 332:323-329, 1988; Presta, *Curr. Op. Struct. Biol.* 2:593-596, 1992; Liu et al, *Proc. Natl. Acad. Sci. USA* 84:3439, 1987; Larrick et al, *Bio/Technology* 7:934, 1989; Winter & Harris, *TIPS* 14:139, 1993; Carter et al, *Proc. Nat. Acad. Sci.* 89:4285 1992). Similarly, to create a primatized antibody the murine CDR regions can be inserted into a primate framework using methods known in the art (see e.g. WO 93/02108 and WO 99/55369).

Alternatively, a humanized antibody may be created by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al, *Mol. Immunol.* 28:489-498, 1991 and Pedersen et al, *J. Mol. Biol.* 235:959-973, 1994). Therefore, it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system. This procedure of humanization is referred to as "veneering" because only the surface of the antibody is altered, the supporting residues remain undisturbed.

Further, WO 2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies.

The CDRs of a given antibody may be readily identified, for example using the system described by Kabat et al in *Sequences of Proteins of Immunological Interest*, 5th Ed., US Department of Health and Human Services, PHS, NIH, NIH Publication No. 91-3242, 1991).

In a preferred embodiment, the antibodies for use in the present invention are human monoclonal antibodies. Such human monoclonal antibodies directed against G-CSF or its receptor can be generated using transgenic or transchromosomic mice carrying parts of the human immune system rather than the mouse system. These transgenic and transchromosomic mice include mice referred to herein as HuMAb mice and KM mice.

Still further, alternative transgenic animal systems expressing human immunoglobulin genes are available in the art and can be used to raise antibodies. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and can be used to raise antibodies against G-CSF or its receptor. For example, mice carrying both a human heavy chain transchromosome and a human light chain transchromosome, referred to as "TC mice" can be used; such mice are described in Tomizuka et al, *Proc. Natl. Acad. Sci. USA* 97:722-727, 2000.

Human monoclonal antibodies can also be prepared using phage display methods for screening libraries of human immunoglobulin genes. Such phage display methods for isolating human antibodies are established in the art. See for example: U.S. Pat. Nos. 5,223,409; 5,403,484; and 5,571, 698; U.S. Pat. Nos. 5,427,908 and 5,580,717; U.S. Pat. Nos. 5,969,108 and 6,172,197 and U.S. Pat. Nos. 5,885,793; 6,521,404; 6,544,731; 6,555,313; 6,582,915 and 6,593,081.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767.

The αG-CSF antibodies of the present invention also include antigen-binding fragments such as Fv, Fab, Fab' and F(ab')$_2$ fragments. Traditionally, antigen-binding fragments were generated by the proteolytic digestion of full antibodies (Morimoto et al, *Journal of Biochemical and Biophysical Methods* 24:107-117, 1992; Brennan et al, *Science* 229:81, 1985). A number of recombinant methods have now been developed for producing antigen-binding fragments of antibodies directly in recombinant host cells.

For example, Fab'-SH fragments can be directly recovered from *E. coli* and chemically coupled to form F(ab')$_2$ fragments (Carter et al, *Bio/Technology* 10:163-167, 1992). F(ab')$_2$ fragments can also be formed using the leucine zipper GCN4 to promote assembly of the F(ab')$_2$ molecule. Fv, Fab or F(ab')$_2$ fragments can also be isolated directly from recombinant host cell cultures. A number of recombinant methods have been developed for the production of single chain antibodies including those described in U.S. Pat. No. 4,946,778; Bird, *Science* 242:423, 1988, Huston et al, *Proc. Natl. Acad. Sci. USA* 85:5879, 1988 and Ward et al, *Nature* 334:544, 1989. Single chain antibodies may be formed by linking heavy ($V_H$) and light ($V_L$) chain variable region (Fv region) fragments via an short peptide linker to provide a single polypeptide chain (scFvs). The scFvs may also form dimers or trimers, depending on the length of a peptide linker between the two variable regions (Kortt et al, *Protein Engineering* 10:423, 1997). Phage display is another well known recombinant method for producing the antigen-binding fragments of the present invention.

The antigen-binding fragments of the present invention may be screened for desired properties. The assays described herein provide the means to identify antigen-binding fragments that bind to G-CSF or G-CSFR and which antagonize G-CSF signaling through G-CSFR.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9. cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention from host cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

Antibodies expressed by different cell lines or in transgenic animals may have different glycosylation patterns from each other. However, all such antibodies to G-CSF or its receptor used in the treatment of chronic immune-mediated inflammatory pulmonary conditions are part of the present invention, regardless of the glycosylation pattern of the antibodies.

Techniques are also known for deriving an antibody of a different subclass or isotype from an antibody of interest, i.e. subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g. DNA encoding the constant region of an antibody of the desired isotype.

Vectors available for cloning and expression in host cell lines are well known in the art, and include but are not limited to vectors for cloning and expression in mammalian cell lines, vectors for cloning and expression in bacterial cell lines, vectors for cloning and expression in phage and vectors for cloning and expression insect cell lines. The antibodies can be recovered using standard protein purification methods.

In a preferred embodiment, antibodies for use in the method of the present invention are human or humanized αG-CSF antibodies which antagonize G-CSF signaling via G-CSFR.

Preferably, the human or humanized αG-CSF antibodies are in isolated, homogenous or fully or partially purified form.

More preferably, the human or humanized αG-CSF antibodies are full-length monoclonal antibodies or antigen-binding fragments.

As indicated above, the selection of antigen-binding fragments or modified forms of the antibodies may be influenced by the effect the fragments or modified forms have on the individual half-life.

Another example of a useful agent is a soluble form of the G-CSFR which competes with the naturally occurring membrane-associated G-CSFR for G-CSF interaction. Those skilled in the art can readily prepare soluble forms of the receptor, see for example U.S. Pat. No. 5,589,456 and Honjo et al.

Alternatively, agents can be screened for their ability to bind to G-CSF or G-CSFR-genetic materials. In one embodiment, G-CSF- or G-CSFR-encoding cDNA or genomic DNA or mRNA transcript or portion thereof such as an EST or SAGE tag is immobilized to a solid support such as a nanoparticle or microsphere. Potential agents are then brought into contact with the immobilized nucleic acid molecules and binding detected by change in radiation, emissions, atom excitation, mass and/or density.

Once identified, the agent is eluted off the nucleic acid molecule and characterized in more detail. For example, agents which bind to G-CSF/G-CSFR genetic material may inhibit expression (transcription and/or translation).

The present invention further contemplates using chemical analogs of G-CSF or G-CSFR as antagonists of G-CSF or its receptor. As indicated above, soluble G-CSF receptors may also be employed.

Chemical analogs contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogs.

Other agents contemplated by the present invention include nucleic acid molecules such as RNA or DNA which are useful for inducing silencing by antisense- or sense-mediated mechanisms of genes encoding the cytokines or their receptors. Sense-mediated gene silencing is also referred to as co-suppression and involves a range of mechanisms including the induction of RNAi. Transcriptional and post transcriptional gene silencing is therefore, contemplated by the present invention.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as the morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. α-anomeric nucleic acids, etc.). Also included are synthetic molecules that mimic polynucleotides in their ability to bind to a designated sequence via hydrogen binding and other chemical interactions. Such molecules are known in the art and include, for example, those in which peptide linkages substitute for phosphate linkages in the backbone of the molecule.

Antisense polynucleotide sequences, for example, are useful in silencing transcripts of the G-CSF genetic sequence or the G-CSFR genetic sequence (see Geng et al, *Molecular Immunology* 44:5121-529, 2007). Furthermore, polynucleotide vectors containing all or a portion of the G-CSF gene locus may be placed under the control of a promoter in either the sense or antisense orientation and introduced into a cell. Expression of such a sense or antisense construct within a cell interferes with target transcription and/or translation. Furthermore, co-suppression (i.e. using sense-suppression) and mechanisms to induce RNAi or siRNA may also be employed. Alternatively, antisense or sense molecules may be directly administered. In this latter embodiment, the antisense or sense molecules may be formulated in a composition and then administered by any number of means to target cells.

A variation on antisense and sense molecules involves the use of morpholinos, which are oligonucleotides composed of morpholine nucleotide derivatives and phosphorodiamidate linkages (for example, Summerton and Weller, *Antisense and Nucleic Acid Drug Development* 7:187-195, 1997).

In one embodiment, the present invention employs compounds such as oligonucleotides and similar species for use in modulating the function or effect of nucleic acid molecules encoding G-CSF or G-CSFR, i.e. the oligonucleotides induce transcriptional or post-transcriptional gene silencing. This is accomplished by providing oligonucleotides which specifically hybridize with one or more nucleic acid molecules encoding the target nucleic acid. The oligonucleotides may be provided directly to a cell or generated within the cell. As used herein, the terms "target nucleic acid" and "nucleic acid molecule encoding G-CSF or G-CSFR" have been used for convenience to encompass the encoding DNA, RNA (including pre-mRNA and mRNA or portions thereof) transcribed from such DNA, and also cDNA derived from such RNA. The hybridization of a compound of the subject invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired.

"Complementary" as used herein, refers to the capacity for precise pairing between two nucleobases of an oligomeric compound. For example, if a nucleobases at a certain position of an oligonucleotide (an oligomeric compound), is capable of hydrogen bonding with a nucleobases at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products.

In the context of the subject invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those herein described.

For topical delivery of antisense compounds, these oligonucleotides may contain modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Sense and antisense nucleotides sequences contemplated herein particularly include 20 to nucleotide bases in length. Reference to "20 to 30" includes 20, 21, 22, 23, 24, 25, 26, 27, 28, 29 or 30 or their equivalents outside the range 20 to 30 nucleobases. The terms "nucleobases" and "nucleotides" may be used interchangeably. Particularly useful sense and antisense molecules are directed to the G-CSF gene or mRNA (SEQ ID NOs:2 and 3) encoding the mature protein (SEQ ID NO:4) or to the G-CSFR gene or mRNA (SEQ ID NOs:6 and 7) encoding the mature protein (SEQ ID NO:8).

Whilst sense or antisense molecules directed to the G-CSF gene or mRNA or G-CSFR gene or mRNA sense or antisense molecules are contemplated against any portion of the coding or non-coding regions including leader sequence and selected introns or extons of the G-CSF or G-CSFR gene or mRNA. Hence, sense and antisense molecules of 20 to 30 nucleotide basis in length are contemplated to one or more of SEQ ID NOs:2, 3, 6 or 7.

In an alternative embodiment, genetic constructs including DNA "vaccines" are used to generate antisense or sense molecules mammalian cells. Furthermore, many of the preferred features described above are appropriate for sense nucleic acid molecules.

This aspect of the present invention can be worked implemented by conventional molecular biology and recombinant DNA techniques. The techniques are well known in the art and are described in various publications, such as Sambrook, Fritsch & Maniatis, *Molecular Cloning: A Laboratory Manual*, Second Edition (1989) Cold Spring Harbor Laboratory Press, Cold Spring Harbor, N.Y.; DNA Cloning: *A Practical Approach*, Volumes I and II, D. N. Glover ed. 1985 and Ausubel et al. (eds.), *Current Protocols in Molecular Biology*, John Wiley & Sons, Inc., 1994.

Nucleic acids of the present invention may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is a DNA regulatory region capable of binding an RNA polymerase in a cell and initiating transcription of a coding sequence. A promoter sequence is generally bounded at its 3' terminus by the transcription initiation site and extends upstream in the 5' direction to include the minimum number of bases or elements necessary to initiate transcription at any level. A transcription initiation site as well as protein binding domains (consensus sequences) responsible for the binding of RNA polymerase may be found within the promoter sequence. The promoter may be operably associated with other expression control sequences, including enhancer and repressor sequences or with a nucleic acid of the invention. Promoters which may be used to control gene expression include, but are not limited to, cytomegalovirus (CMV) promoter and the SV40 early promoter region.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The terms "express" and "expression" mean allowing or causing the information in a gene, RNA or DNA sequence to be converted into a product; for example, producing a protein by activating the cellular functions involved in transcription and translation of a nucleotide sequence. A DNA sequence is expressed in or by a cell to form an "expression product" such as RNA (such as mRNA or a double stranded short RNA, hairpin RNA or antisense RNA) or a protein (such as an antagonist of cytokine activity or portion of an anti-cytokine antibody). The expression product itself may also be said to be "expressed" by the cell.

The terms "vector", "cloning vector" and "expression vector" mean the vehicle (such as a plasmid) by which a DNA or RNA sequence can be introduced into a host cell, so as to transform the host and, optionally, promote expression and/or replication of the introduced sequence.

The term "transfection" or "transformation" means the introduction of a nucleic acid into a cell. These terms may refer to the introduction of a nucleic acid encoding a cytokine cross-reactive antibody or a fragment thereof into a cell. A host cell that receives the introduced DNA or RNA has been "transformed" and is a "transformant" or a "clone". The DNA or RNA introduced to a host cell can come from any source, including cells of the same genus or species as the host cell, or cells of a different genus or species.

The term "host cell" means any cell of any organism that is selected, modified, transfected, transformed, grown, or used or manipulated in any way, for the production of a substance by the cell, for example the expression of a protein or the replication of a gene.

The term "expression system" means a host cell and compatible vector which, under suitable conditions, can express a protein or nucleic acid which is carried by the vector and introduced to the host cell. Common expression systems include E. coli host cells and plasmid vectors, insect host cells and Baculovirus vectors, and mammalian host cells and vectors.

Agents (e.g. antibodies, proteins such as non-signalling mutant forms of G-CSF, small chemical molecules, soluble receptors, etc) identified in accordance with the present invention are conveniently supplied in pharmaceutical compositions.

Composition forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the modulator is suitably protected, it may be orally administered, for example, with an inert diluent or with an assimilable edible carrier, or it may be enclosed in hard or soft shell gelatin capsule, or it may be compressed into tablets, or it may be incorporated directly with the food of the diet or administered via breast milk. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of modulator. The percentage of the compositions and preparations may, of course, be varied and may conveniently be between about 5 to about 80% of the weight of the unit. The amount of modulator in such therapeutically useful compositions is such that a suitable dosage will be obtained. Preferred compositions or preparations according to the present invention are prepared so that an oral dosage unit form contains between about 0.1 µg and 200 mg of modulator. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules, creams and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and anti-fungal agents, isotonic and absorption delaying agents and the like. The use of such media and agents for pharmaceutical active agents is well known in the art and except insofar as any conventional media or agent is incompatible with the modulator, their use in the therapeutic compositions is contemplated. Supplementary active compounds can also be incorporated into the compositions.

As indicated above, administration may be by any means. For the treatment of pulmonary inflammatory conditions intra-nasal, intravenous and intra-pulmonary administration is particularly efficacious.

Dosage regimens may be adjusted to provide the optimum desired response (e.g. a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the αG-CSF antibody of the present invention, employed in the pharmaceutical composition at levels lower than that required in order to achieve the desired therapeutic effect and gradually increase the dosage until the desired effect is achieved. In general, a suitable daily dose of a composition of the invention may be that amount of the compound which is the lowest dose effective to produce a therapeutic effect. Such an effective dose will generally depend upon the factors described above. It is preferred that administration be by injection, preferably proximal to the site of the target (e.g. lung). If desired, the effective daily dose of a pharmaceutical composition may be administered as two, three, four, five, six or more subdoses administered separately at appropriate intervals throughout the day.

For therapeutic applications, the αG-CSF antibodies of the present invention are administered to a mammal, preferably a human, in a pharmaceutically acceptable dosage form such as those discussed above, including those that may be administered to a human intravenously as a bolus or by continuous infusion over a period of time by intra-pulmonary, nasal, oral or intra-arterial routes.

The composition may also comprise genetic molecules such as a vector capable of transfecting target cells where the vector carries a nucleic acid molecule capable of encoding a modulator, when the modulator is a proteinaceous molecule. The vector may, for example, be a viral vector. In this regard, a range of gene therapies are contemplated by the present invention including isolating certain cells, genetically manipulating and returning the cell to the same subject or to a genetically related or similar subject.

Hence, the present invention contemplates a further aspect of the present invention contemplates a method for the treatment of a pulmonary condition characterized by or associated with infiltration of neutrophils in a subject, said method comprising administering to said subject an amount of an agent effective to inhibit the activity of G-CSF or G-CSFR or inhibit expression of the gene encoding G-CSF or G-CSFR.

Another aspect provides a method for treating a pulmonary disease associated with neutrophil infiltration in a subject, said method comprising administering to said subject a G-CSF or G-CSFR inhibiting agent selected from the group consisting of:

a. an antibody specific for G-CSF;
b. an antibody specific for G-CSFR;
c. a soluble G-CSFR or a G-CSF-binding portion thereof;
d. a sense or antisense molecule 20 to 30 nucleobases in length targeted to a nucleic acid molecule encoding G-CSF, wherein the nucleotide sequence comprises the sequence set forth in SEQ ID NO:3; and
e. a sense or antisense molecule 20 to 30 nucleobases in length targeted to a nucleic acid molecule encoding a G-CSFR, wherein the nucleotide sequence comprises the sequence set forth in SEQ ID NO:7.

In another aspect, the present invention is directed to a method for the treatment of COPD or an exacerbated form thereof or a related condition or a complication arising from same or a manifestation thereof in a subject said method comprising administering to said subject an amount of an agent effective to inhibit the activity of G-CSF or G-CSFR or inhibit expression of the gene encoding G-CSF or G-CSFR.

Another aspect of the present invention relates to a method for the treatment of a pulmonary condition characterized by or associated with infiltration of neutrophils such as but not limited to COPD or an exacerbated form thereof such as AECOPD, a related condition or a complication arising therefrom or a manifestation thereof in a subject, said method comprising administering an agent which inhibits the activity of G-CSF or G-CSFR or inhibits the expression of the gene encoding G-CSF or G-CSFR and at least one other therapeutic agent such as an anti-inflammatory, a bronchodilator or an antibiotic.

In a particularly preferred embodiment, the present invention contemplates a method for the treatment of COPD or an exacerbated form thereof or a related condition or a complication arising from same or a manifestation thereof in a subject said method comprising administering to said subject an amount of an antibody or antigen-binding portion thereof effective to inhibit the activity of G-CSF or G-CSFR.

The present invention further contemplates the use of an agent which inhibits the activity of G-CSF or G-CSFR, or which inhibits the expression of the gene encoding G-CSF or G-CSFR in the manufacture of a medicament in the treatment of a pulmonary condition characterized by or associated with infiltration of neutrophils in a subject.

Still a further aspect contemplates the use of an agent which inhibits the activity of G-CSF or G-CSFR or which inhibits expression of a gene encoding G-CSF or G-CSFR in the manufacture of a medicament for treating a pulmonary disease associated with neutrophil infiltration in a subject, wherein said agent is selected from the group consisting of:

a. an antibody specific for G-CSF;
b. an antibody specific for G-CSFR;
c. a soluble G-CSFR or a G-CSF-binding portion thereof;
d. a sense or antisense molecule 20 to 30 nucleobases in length targeted to a nucleic acid molecule encoding G-CSF, wherein the nucleotide sequence comprises the sequence set forth in SEQ ID NO:3; and
e. a sense or antisense molecule 20 to 30 nucleobases in length targeted to a nucleic acid molecule encoding a G-CSFR, wherein the nucleotide sequence comprises the sequence set forth in SEQ ID NO:7.

In a preferred embodiment, the present invention is directed to the use of an antibody to G-CSF or G-CSFR in the manufacture of a medicament for the treatment of COPD or an exacerbated form thereof or a related condition or a complication arising from same or a manifestation thereof in a subject.

Animal models useful for testing inhibition of G-CSF or its receptor, or other approaches to antagonism of G-CSF activity, include acute LPS exposure, sub-chronic cigarette smoke exposure and influenza infection of smoke-exposed mice (exacerbation model).

In these models, neutrophilic inflammation, TNFα production and excessive protease activity enable the determination of the effectiveness of αG-CSF/αG-CSFR antibodies or other antagonists, or reduced G-CSF levels or G-CSF signalling, in suppressing some of the key features of COPD-like inflammation.

Neutrophils are a major predominant cell type infiltrating the airways of COPD patients (Beeh and Beier, *Clin Exp Allergy* 26(2):142-157, 2006; Stockley, *Chest* 121(5 *Suppl*): 151S-155S, 2002). The ability of neutrophils to generate reactive oxygen species and proteases is critical to their host defence role. However, as with all aspects of the immune response, over-activity can be detrimental.

The cytokine milieu present in the airways of COPD sufferers provides the ideal environment for enhanced neutrophilic inflammation (Barnes, *N Engl J Med* 343(4):269-280, 2000; Barnes, *Cytokine Growth Factor Rev* 14(6):511-522, 2003). Since neutrophil survival in the healthy lung is normally very limited, the prolonged life of neutrophils in COPD is an important feature.

In accordance with the present invention, suppression of G-CSF with a test antagonist had a significant impact on neutrophil number in the BALF and blood induced by LPS, cigarette smoke exposure and influenza infection. As neutrophils are key mediators of COPD-like inflammation, the significant reduction in neutrophil numbers induced by the G-CSF antagonist in all three COPD models indicates that the antagonism of G-CSF activity is a useful therapeutic approach.

The present invention is further described by the following non-limiting Examples. In the Examples the following methods are employed.

Animals

Specific pathogen-free male Balb/C mice aged 7 weeks and weighing ~20 g were obtained from the Animal Resource Centre Pty. Ltd. (Perth, Australia). The animals were housed at 20 C on a 12-h day/night cycle in sterile micro-isolators and fed a standard sterile diet of Purina mouse chow with water allowed ad libitum.

Cigarette Smoke Exposure

Mice were placed in an 18 liter perspex chamber in a class II biosafety cabinet and exposed to cigarette smoke. Mice were exposed to cigarette smoke generated from 9 cigarettes per day for 4 days, delivered three times per day at 8.00 am, 12 noon and 4 pm using 3 cigarettes spaced over one hour. In pilot experiments, it was found that 3, 6 and 9 cigarettes per day are very well tolerated. Sham-exposed mice were placed in an 18 liter perspex chamber but do not receive cigarette smoke. On the fifth day, mice were killed by an intraperitoneal (i.p.) overdose of anaesthetic (5.6 mg ketamine/1.12 mg xylazine, Parnell Laboratories, NSW, Australia) and the lungs lavaged with PBS. Commercially available filter-tipped cigarettes (manufactured by Philip Morris, Australia) of the following composition were used: 16 mg or less of tar, 1.2 mg or less of nicotine and 15 mg or less of CO. Smoke was generated in 50 ml tidal volumes over 10 s using timed draw-back mimicking normal smoking inhalation volume and cigarette burn rate. Group sizes of 8 mice per treatment were used to ensure the study was powered to detect differences in response variable at the 0.05 confidence level.

Drug Administration

Mice were given the specified doses of PBS, isotype control or anti-GSCF antibody (as outlined in section 1) once daily (60 minutes prior to first smoke), administered by i.p. injection.

Virus Infection

Mice exposed to cigarette smoke (as described above) are infected with a non-lethal, mouse adapted influenza strain [Mem71, H3N1] at a dose known (in normal mice) to cause productive replication and inflammation, but no overt disease. Mice are dissected 3 d and 10 d after influenza infection. Control mice receive a preparation of uninfected cells used to grow the virus.

Bronchoalveolar Lavage (BAL)

BAL was performed in terminally anaesthetized mice. Briefly, lungs from each mouse were lavaged in situ with a 400 μl aliquot, followed by three 300 μl of PBS, with approximately 1 ml of bronchoalveolar lavage fluid (BALF) recovered from each animal. Smoke exposure had no effect on the recovered volume. The total number of viable cells in the BALF was determined by using the fluorophores ethidium bromide and acridine orange (Molecular Probes, San Diego, USA) on a standard Neubauer hemocytometer using a Zeiss Axioscope Fluorescence microscope. Cytospins were prepared using 200 μl BALF at 350 rpm for 10 min on a Cytospin 3 (Shandon, UK). Cytospin preparations were stained with DiffQuik (Dade Baxter, Australia) and cells identified and differentiated into mononuclear, epithelial, eosinophils, neutrophils and macrophages by standard morphological criteria. A minimum of 500 cells per slide were counted.

Enzyme Linked Immunosorbant Assays (ELISAs)

TNFα concentrations in BALF samples were measured using Pharmingen OptEIA (Trademark) ELISA kits (Pharmingen) as per manufacturer's instructions. The absorbances were read at 450 nm (Victor 1420 Multilabel Counter, Wallac), and analysed using the Microplate Manager (Registered) (BioRad, USA) program, which derived the standard curve and sample absorbances.

Protease Expression and Activity in BALF

Zymography was used to assess protease expression. Briefly, BALF from animals in each treatment group were pooled and concentrated by adding 250 μl of 50% v/v trichloroacetic acid to 500 μl of pooled BALF samples and left at 4° C. overnight. The next day samples were spun (13,000 rpm for 10 min, at 4° C.) and the pellet washed twice with 300 μl 80% diethyl ether (in 20% v/v ethanol) and dried in air for 10 min. The pellet was then resuspended in 50 μl of 1× non-reducing buffer, heated for 10 min at 65° C. and 20 μl loaded on SDS-page mini-gels. SDS-page mini-gels (10% v/v) were prepared with the incorporation of gelatin (2 mg/ml) before casting. BALF (20 μl) was run into gels at a constant voltage of 200 V under non-reducing conditions. When the dye front reached the bottom, gels were removed and washed twice for 15 min in 2.5% v/v Triton X-100 and incubated at 37° C. overnight in zymography buffer (50 mM Tris-HCl (pH 7.5), 5 mM $CaCl_2$, 1 mM $ZnCl_2$ and 0.01% v/v $NaN_3$). The gels were then stained for 45 min with Coomassie Brilliant Blue R-250 and extensively destained. Following destaining, zones of enzyme activity appeared clear against the Coomassie Blue background.

Neat BALF was also tested for net gelatinase and net serine protease activity using fluorescence-conjugated gelatin (Molecular Probes, USA) and N-methoxysuccinyl-ala-ala-pro-val-p-Nitroanilide (Sigma, USA), respectively. The gelatin substrate (10 μg) was diluted in 50 mM Tris pH 7.5, 150 mM NaCl, 5 mM $CaCl_2$, 0.01% v/v $NaN_3$ and incubated at room temperature for 16 h with 100 μl of neat BALF. The digested substrate had absorption/emission maxima at 495 nm/515 nm. The N-methoxysuccinyl-ala-ala-pro-val-p-Nitroanilide substrate (50 µg) was diluted in 50 mM Tris pH 7.5, 150 mM NaCl, 5 mM $CaCl_2$, 0.01% $NaN_3$ and incubated at room temperature for 16 h with 100 µl of neat BALF. The digested substrate had absorption maxima at 405 nm. The fluorescence intensity of the substrates was measured in a microplate reader (Victor II, Wallac) to detect quantitative differences in activity.

Virus Quantitation

Whole lungs were removed from 4 mice per treatment group and weighed. Lungs were homogenized in maintenance medium, with 2×15 sec pulses, followed by a low speed clearing spin. Serial dilutions of lung homogenate were then used in plaque assays as previously described (Youil, *J Virol Methods* 120(1):23-31, 2004) and viral titres were expressed as pfu/g lung.

Histology

To ensure consistent morphological preservation of lungs, mice were killed by intraperitoneal anaesthesia (5.6 mg ketamine/10.12 mg xylazine) overdose and then perfusion fixed via a tracheal cannula with 4% v/v formaldehyde at exactly 200 mm $H_2O$ pressure. After 1 h, the trachea was ligated, the lungs were removed from the thorax and immersed in 4% v/v formaldehyde for a minimum period of 24 h. After fixation of the lung tissue and processing in paraffin wax, sections (3-4 µm thick) were cut transversely through the left lobe. Sections were stained with hematoxylin and eosin (H&E) for general histopathology.

Statistical Analyses

As data were normally distributed, they are presented as grouped data expressed as mean±standard error of the mean (s.e.m.); n represents the number of mice. Differences in total BALF cell types and differential counts were determined by one-way analysis of variance (ANOVA) followed by Dunnett post hoc test for multiple comparisons, where appropriate. In some cases, Student's unpaired t-test was used to determine if there were significant differences between means of pairs. All statistical analyses were performed using GraphPad Prism (Trademark) for Windows (Version 3.03). In all cases, probability levels less than 0.05 (*$P<0.05$) were taken to indicate statistical significance.

EXAMPLE 1

Rationale and Study Design

This is a model of acute lung inflammation where instilled lipopolysaccharide (LPS) induces intense neutrophilic inflammation. Detailed kinetics and the use of anti-GM-CSF antibodies in this model system have previously been published (Bozinovski et al, *J Biol Chem* 277(45):42808-42814, 2002; Bozinovski et al, *Am J Physiol Lung Cell Mol Physiol* 286(4):L877-885, 2004). Under the conditions described below, inflammation in this model is refractory to the glucocorticosteroid dexamethsaone (Bozinovski et al, *J Proteome Res* 4(1):136-145, 2005).

Experimental Design:

Mice were treated with either isotype control or 250 µg/dose ip of αG-CSF at t=−3 hours, exposed to one dose of LPS at t=0, and then dissected 24 hours later (FIG. 1).

(i) Groups:
　Control-no treatment
　Saline
　LPS
　LPS+isotype (Rat IgG1, GL113)
　LPS+αG-CSF (Rat αG-CSF, MAB414)
　Saline+isotype (Rat IgG1, GL113)
　Saline+αG-CSF (Rat αG-CSF, MAB414)

(ii) Endpoints:
　BAL fluid
　　total/differential cell counts
　　ELISAs (TNF alpha)
　　zymography (protease induction)
　　protease activity
　Blood
　　blood smears
　　total/differential cell counts
　Whole lungs
　　snap-frozen and pooled for each group
　The data are of BAL fluid and blood cell counts, graphs of ELISA results, graphs of protease activity and zymography gels. Frozen BAL fluid samples and pooled lung samples have also been retained.

(iii) Mice:
　Male Balb/c mice; 6 weeks of age; approximately 20 grams
　8/group
　56 mice supplied by ARC, Perth.

(iv) Drug Formulation:
　Test compound: αG-CSF antibody (αG-CSF)
　Specificity: mouse G-CSF (neutralises G-CSF bioactivity)
　Ig class: rat IgG1
　Source: R&D Systems
　Catalog number: MAB414
　Clone: 67604
　Endotoxin level: <0.1 EU per 1 µg of mAb, as supplied by R&D.
　Formulation: Supplied as a 0.2 µM filtered solution in PBS at 9.95 mg/mL. Diluted to 1.0 mg/mL with sterile endotoxin free
　PBS. Stored as 5 mg (5 mL) aliquots, at −20 C.
　Dosage: 250 µg/injection/mouse, i.p.
　Test compound: isotype control antibody (isotype)
　Specificity: *E. coli* β-galactosidase
　Ig class: rat IgG1
　Source: Walter and Eliza Hall Institute Monoclonal Antibody Lab
　Clone: GL113
　Endotoxin level: <0.1 EU per 1 µg of mAb, as supplied by WEHI.
　Formulation: Supplied as sterile solution in PBS at 1.3 mg/mL.
　Diluted to 1.0 mg/mL with sterile endotoxin free PBS. Stored in 5 mg (5 mL) aliquots, at −20 C.
　Dosage: 250 µg/injection/mouse, i.p.

Effect of αG-CSF Antibody on Inflammatory Cell Number in BALF of LPS-Treated Mice αG-CSF antibody, isotype control or PBS (saline) did not increase inflammatory cell number in the BALF of saline-treated animals (FIGS. 2a through to d).

LPS caused a significant increase in total cell number (FIG. 2a), neutrophils (FIG. 2c) and lymphocytes (FIG. 2d) in the BALF. The isotype control did not have an effect on inflammatory cell number.

Figure 2:
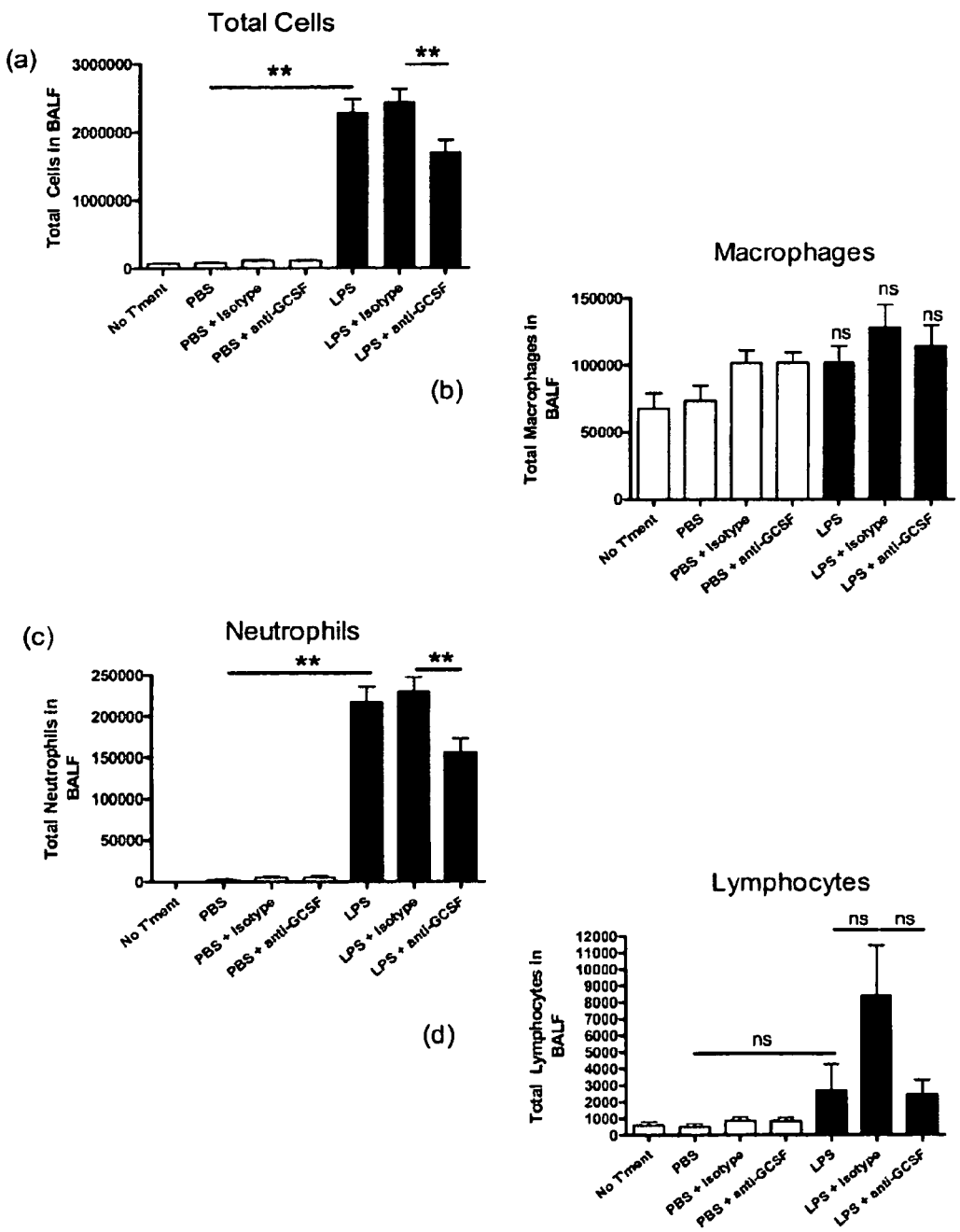
FIGS. 2a through d are graphical representations of total viable cells, macrophages, neutrophils and lymphocytes in BALF of LPS-treated mice after treatment with isotype or αG-CSF antibody. The number of inflammatory cells in the BALF of control, LPS-treated and LPS+αG-CSF antibody-treated animals was determined by standard differential cell analysis. Data are expressed as mean cells/mL BALF of eight animals per group±SEM. $P<0.05$ (annotated by *) are statistically significant, ns=not significant.

In contrast, αG-CSF caused a significant decrease in the total number of cells and the number of neutrophils and lymphocytes, but not macrophages, in LPS-treated animals (FIG. 2).

Figure 3:
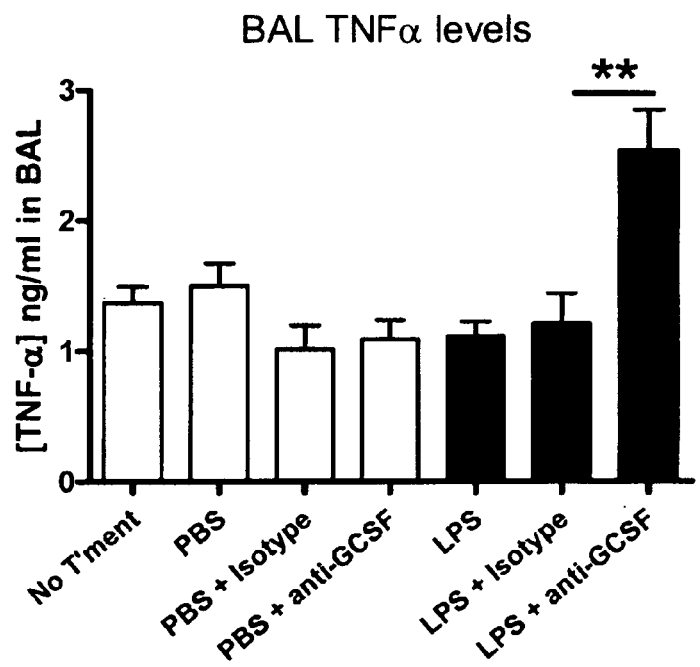
FIG. 3 is a graphical representation protein levels of TNFα in BALF of LPS-treated mice after treatment with isotype or αG-CSF antibody. The protein levels of TNFα in the BALF of control, LPS-treated and LPS+αG-CSF antibody-treated animals were determined by ELISA. Data are expressed as the mean of eight animals per group±SEM. $P<0.05$ (annotated by *) are statistically significant.

Effect of αG-CSF Antibody on Protein Levels of TNFα, in BALF of LPS-Treated Mice, as Determined by ELISAs There was very little TNFα detected in the BALF of saline- or LPS-treated animals at the 24 hour timepoint (FIG. 3). However, it appeared that αG-CSF caused a marked increase in TNFα levels in the BALF of LPS-treated mice.

Figure 4:
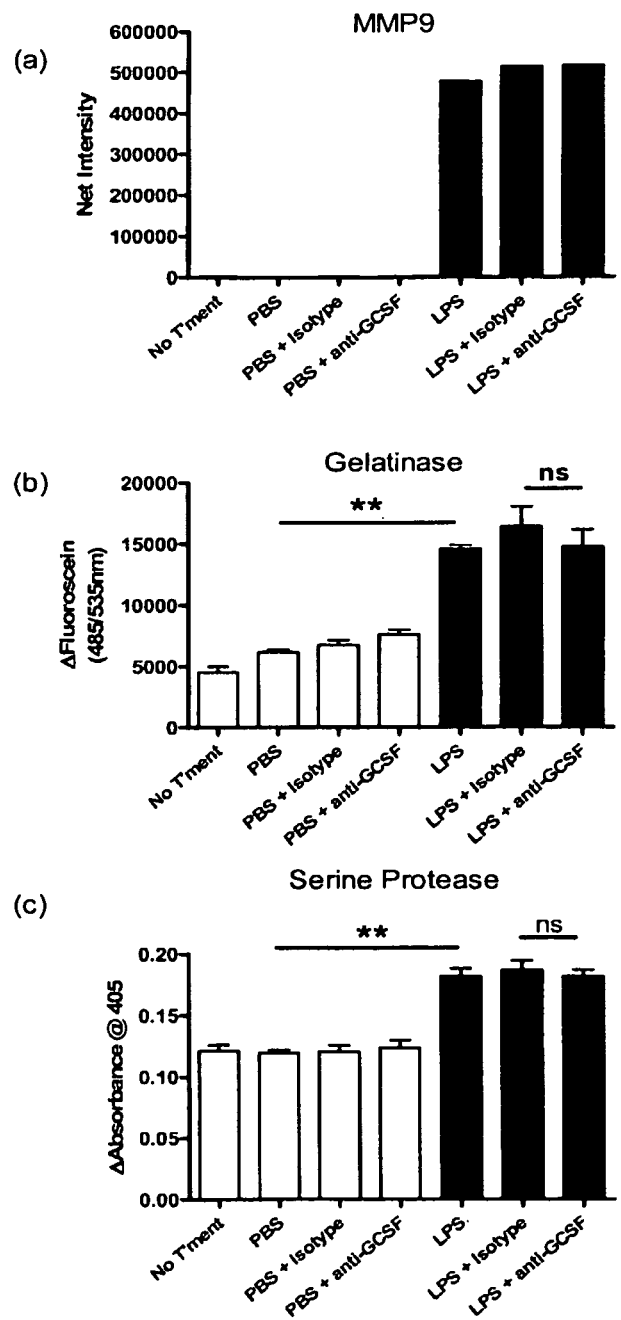
FIGS. 4a through c are graphical representations of MMP9 levels and protease activity in BALF of LPS-treated mice after treatment with isotype or αG-CSF antibody. The levels of MMP9 in the BALF of control, LPS-treated and LPS+αG-CSF antibody-treated animals were determined by zymography. Protease activity in the BALF of treated mice was determined by gelatinase and serine protease assay. Data are expressed as the pooled sample of 8 mice per group (FIG. 3.3a) and the mean of eight animals per group±SEM (FIGS. 3.3b & c). $P<0.05$ (annotated by *) are statistically significant, ns=not significant.
Figure 5:
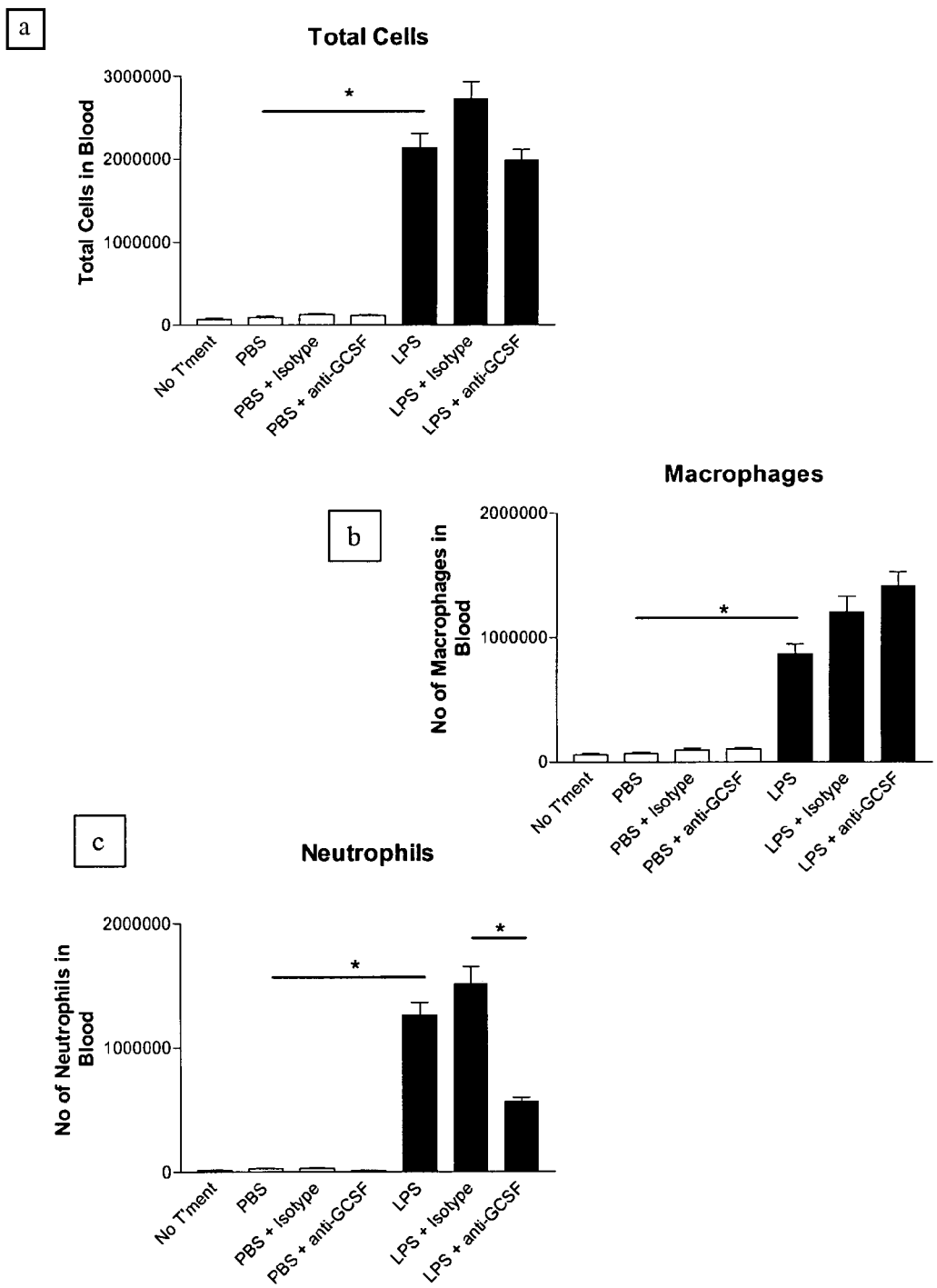
FIGS. 5a through c are graphical representations of total viable cells, macrophages and neutrophils whole blood of LPS-treated mice after treatment with isotype or αG-CSF antibody. The number of inflammatory cells in the whole blood of control, LPS-treated and LPS+αG-CSF antibody-treated animals was determined by standard differential cell analysis. Data are expressed as mean cells/mL BALF of eight animals per group±SEM. $P<0.05$ (annotated by *) are statistically significant.

Effect of αG-CSF Antibody on Protease Expression and Activity in BALF of LPS-Treated Mice, as Determined by Zymography and Protease Assays LPS treatment caused a marked increase in MMP9 expression (FIG. 4a) and protease activity (FIGS. 4b and c) in the BALF of mice. However, there was no effect of either isotype control or αG-CSF on LPS-induced protease expression or activity.

Effect of αG-CSF Antibody on Inflammatory Cell Number in Blood of LPS-Treated Mice LPS caused a significant increase in the number of total viable cells, macrophages and neutrophils in the blood of treated mice. αG-CSF caused a significant reduction in neutrophil number in LPS-treated animals, but did not affect total viable cell or macrophage numbers. Note that there were no lymphocytes detected in the blood of any of the animals.

EXAMPLE 2

Sub-Chronic Smoke

In this model, mice were exposed to smoke (or sham handled) 3 times a day (2 cigarettes/exposure) for 4 days, and analyzed on the fifth day, as previously described (Chen et al, *Neuropsychopharmacology* 30(4), 713-719 2005).

Figure 6:
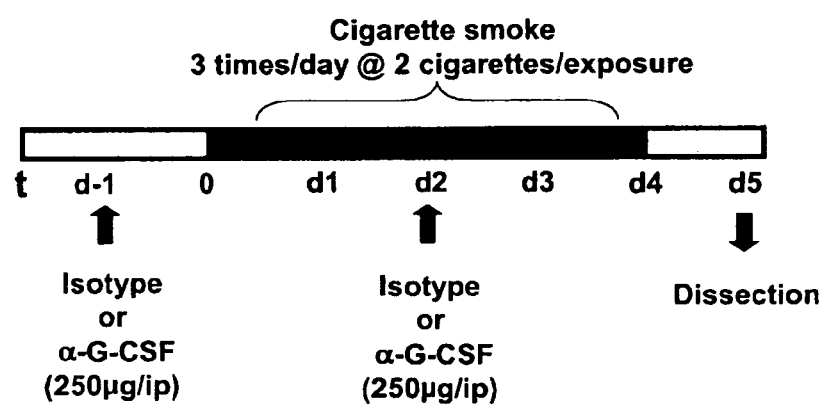
FIG. 6 is a graphical representation showing smoke generated in 50 ml tidal volumes over 10 s using timed draw-back mimicking normal smoking inhalation volume and cigarette burn rate.

Experimental Design:

Mice were exposed to cigarette smoke for 4 days, 3 times per day. Mice were treated with either isotype control or 250 μg/dose ip of αG-CSF at t=d−1 and d2, and then dissected on day 5. Smoke exposure conditions were as previously described (Vlahos et al, *Am J Physiol Lung Cell Mol Physiol* 290(5):L931-945, 2006). Briefly, mice received smoke from 3 cigarettes for 1 h and this was done three times a day for up to 4 days. Commercially available filter-tipped cigarettes (manufactured by Philip Morris, Australia) of the following composition were used: 16 mg or less of tar, 1.2 mg or less of nicotine and 15 mg or less of CO. Smoke was generated in 50 ml tidal volumes over 10 s using timed draw-back mimicking normal smoking inhalation volume and cigarette burn rate (FIG. 6).

(i) Groups:
Sham (handled, but not exposed to smoke)
Sham+isotype (Rat IgG1, GL113)
Sham+αG-CSF (Rat αG-CSF, MAB414)
Smoke alone
Smoke+isotype (Rat IgG1, GL113)
Smoke+αG-CSF (Rat αG-CSF, MAB414)

(ii) Endpoints:
BAL fluid
  total/differential cell counts
  ELISAs (TNF alpha)
  zymography (protease induction)
  protease activity
Blood
  blood smears
  total/differential cell counts
Whole lungs
  snap-frozen and pooled for each group The data are of BAL fluid and blood cell counts, graphs of ELISA results, graphs of protease activity and zymography gels. Frozen BAL fluid samples and pooled lung samples have also been retained.

(iii) Mice Required:
8/group
48 mice (described above)

(iv) Drug Formulation:
Test compound: αG-CSF antibody (described above)
Test compound: isotype control antibody (described above)

Figure 7:
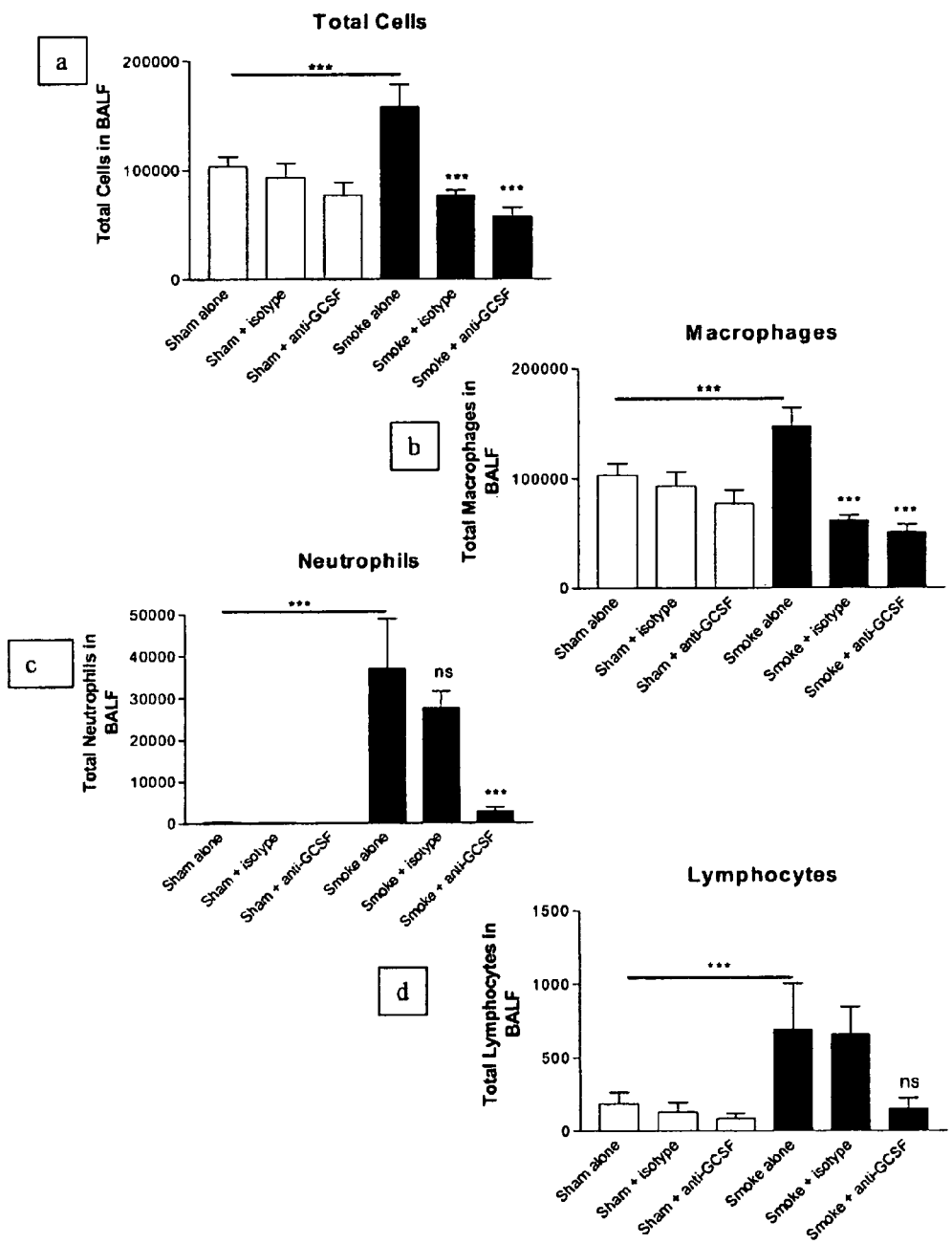
FIGS. 7a through d are graphical representations of total viable cells, macrophages, neutrophils and lymphocytes in BALF of sham or smoke-exposed mice after treatment with isotype or αG-CSF antibody. The number of inflammatory cells in the BALF of control, smoke-exposed and smoke+αG-CSF antibody-treated animals was determined by standard differential cell analysis. Data are expressed as mean cells/mL BALF of 8 animals per group±SEM. $P<0.05$ (annotated by *) are statistically significant, ns=not significant.

Effect of αG-CSF Antibody on Inflammatory Cell Number in BALF of Smoke-Exposed Mice The αG-CSF antibody did not increase the number of inflammatory cells in the BALF of sham mice (FIG. 7).

4-day smoke exposure caused a significant increase in the number of macrophages (FIG. 7b), neutrophils (FIG. 7c) and lymphocytes (FIG. 7d), as well as total cell number (FIG. 7a), in the BALF of mice.

The isotype control reduced total cell number and the number of macrophages and neutrophils in the BALF of smoke-exposed mice, while αG-CSF caused a significant reduction in the number of macrophages, neutrophils and total cells, and a marked reduction in the number of lymphocytes in BALF.

Figure 8:
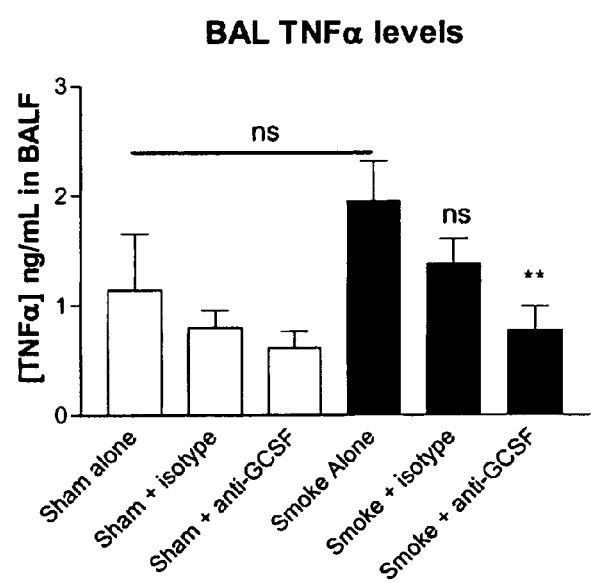
FIG. 8 is a graphical representation of protein levels of TNFα in BALF of sham or smoke-exposed mice after treatment with isotype or αG-CSF antibody. The protein levels of TNFα in the BALF of control, smoke-exposed and smoke+αG-CSF antibody-treated animals were determined by ELISA. Data are expressed as the mean of 8 animals per group±SEM. $P<0.05$ (annotated by *) are statistically significant.

Effect of αG-CSF Antibody on Protein Levels of TNFα, in BALF of Smoke-Exposed Mice, as Determined by ELISAs While there were low levels of TNFα detectable in the BALF of sham-treated animals (FIG. 8), cigarette smoke exposure caused a marked increase in TNFα levels. The isotype control caused a slight reduction and αG-CSF caused a significant reduction in TNFα levels in the BALF of smoke-exposed mice.

Figure 9:
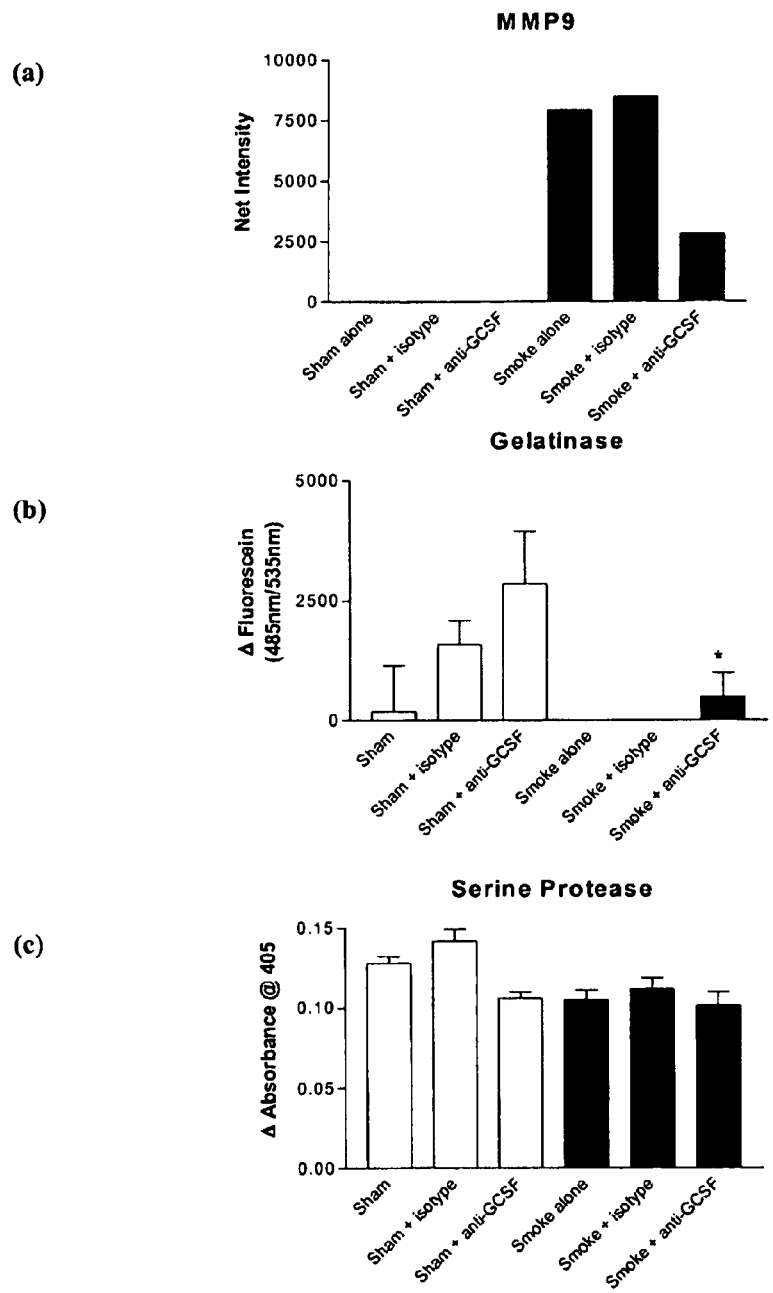
FIGS. 9a through c are graphical representations of MMP9 levels and protease activity in BALF of sham or smoke-exposed mice after treatment with isotype or αG-CSF antibody. The levels of MMP9 in the BALF of control, LPS-treated and LPS+αG-CSF antibody-treated animals were determined by zymography. Protease activity in the BALF of treated mice was determined by gelatinase and serine protease assay. Data are expressed as the pooled sample of 8 mice per group and the mean of eight animals per group±SEM.
Figure 10:
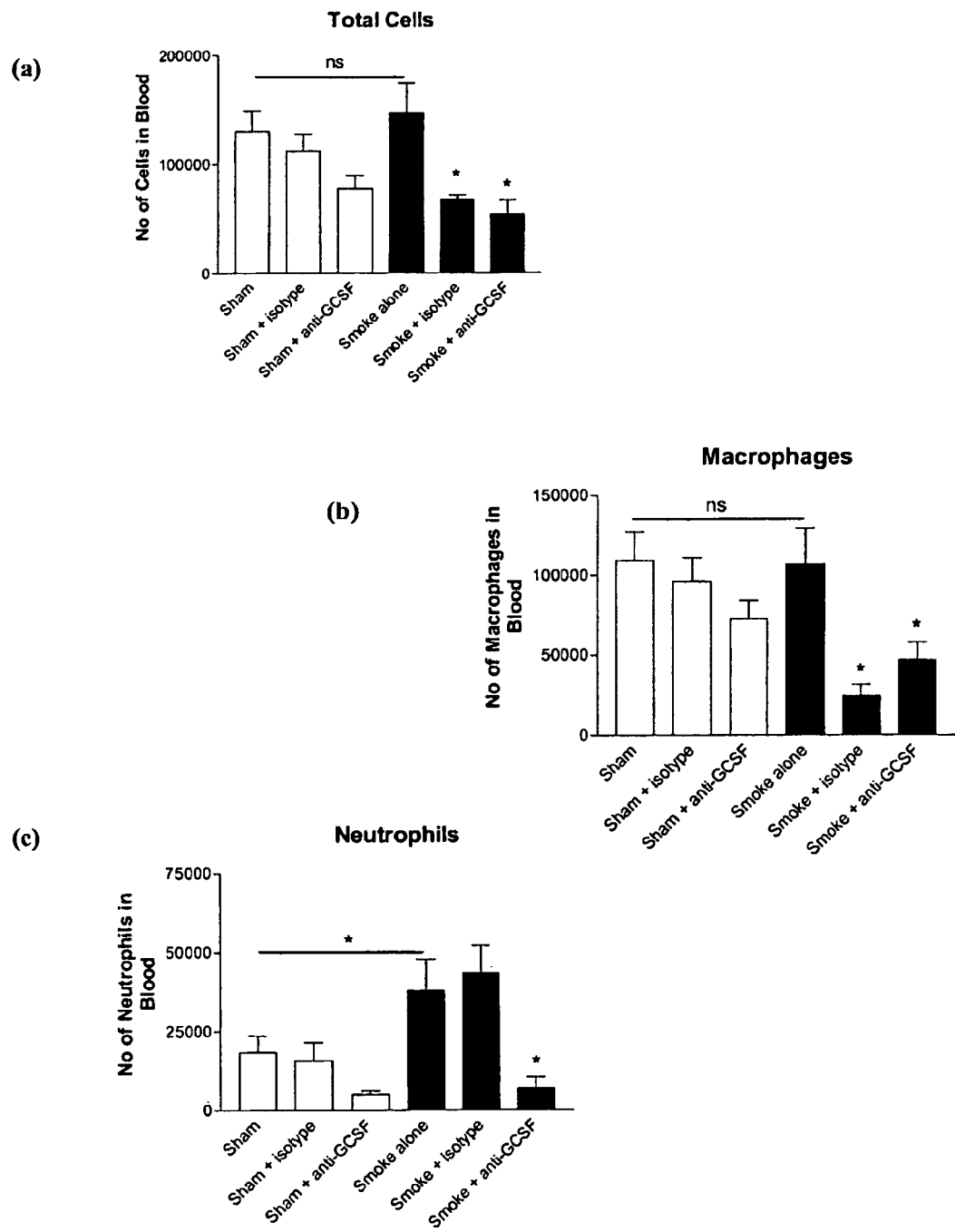
FIGS. 10a through c are graphical representations of total viable cells, macrophages and neutrophils whole blood of sham or smoke-exposed mice after treatment with isotype or αG-CSF antibody. The number of inflammatory cells in the BALF of control, smoke-exposed and smoke+αG-CSF antibody-treated animals was determined by standard differential cell analysis. Data are expressed as mean cells/mL BALF of eight animals per group±SEM. $P<0.05$ (annotated by *) are statistically significant, ns=not significant.
Figure 11:
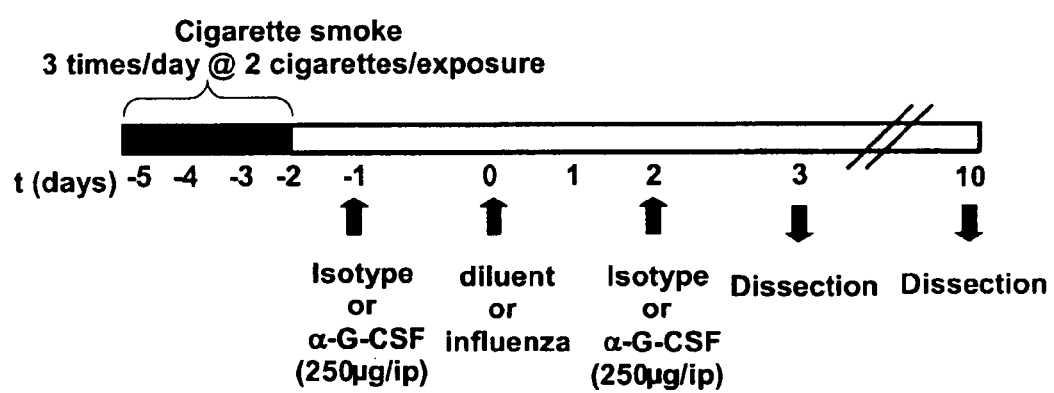
FIG. 11 is a graphical representation showing mice treated with either isotype control or 250 µg/dose ip of αG-CSF at t=d−1 and d2, and then dissected on day 3 or day 10.

Effect of αG-CSF Antibody on Protease Expression and Activity in BALF of Smoke-Exposed Mice, as Determined by Zymography and Protease Assays There was a significant increase in MMP9 expression in the BALF of smoke-exposed mice which was reduced by αG-CSF but not isotype control (FIG. 9a).

In contrast, there was no significant increase in either gelatinase (FIG. 9b) or serine protease activity (FIG. 9c) after smoke exposure. There was no discernable effect of the isotype control or αG-CSF on serine protease activity, although αG-CSF appeared to cause a significant increase in gelatinase activity.

Effect of αG-CSF Antibody on Inflammatory Cell Number in Blood of Smoke-Exposed Mice Smoke exposure caused a significant increase in neutrophil numbers in the blood, compared to sham-treated animals. Note that there were no lymphocytes detected in the blood of any of the animals.

The isotype control caused a significant reduction in total cell number and the number of macrophages in the blood of smoke-exposed animals, while αG-CSF antibody caused a significant reduction in total cell, neutrophil and macrophage numbers in smoke-exposed animals.

EXAMPLE 3

Smoke and Influenza (Exacerbation) Study

Experimental Design:

Mice were exposed to cigarette smoke for 4 days, 3 times per day (day-5 to day-2). Mice were then infected with influenza (MDCK cell-derived Mem-71, influenza A strain) or diluent (uninfected MDCK cell preparation) on day 0. Mice were treated with either isotype control or 250 μg/dose ip of αG-CSF at t=d−1 and d2, and then dissected on day 3 or day 10.

(i) Groups:
1. Control-no treatment (×2)
2. Diluent (×2)
3. Diluent+isotype (×2)
4. Diluent+αG-CSF (×2)

5. Influenza (×2)
6. Influenza+isotype (×2)
7. Influenza+αG-CSF (×2)
(ii) Endpoints:
BAL fluid
total/differential cell counts
ELISAs (TNF alpha)
zymography (protease induction)
protease activity
Blood
blood smears
total/differential cell counts
Whole lungs
lung viral quantitation
PFA-fixed lungs for histology (Grp1, 5, 6, 7 only)
snap-frozen and pooled for each group The data are of BAL fluid and blood cell counts, graphs of ELISA results, lung viral titres, graphs of protease activity and zymography gels. Quantitative lung histology results and histology slides has been provided for control and influenza-treated groups at both timepoints. Frozen BAL fluid samples and pooled lung samples have also been retained.

(iii) Mice Required:
12/group (ie 8 for BAL and 4 for viral titration in whole lungs)
Additional 4/group in Grp1, 5, 6, 7 for histology
184 mice (as described in section 1.1)

(iv) Drug Formulation:
Test compound: αG-CSF antibody (described above)
Test compound: isotype control antibody (described above)

Figure 12:
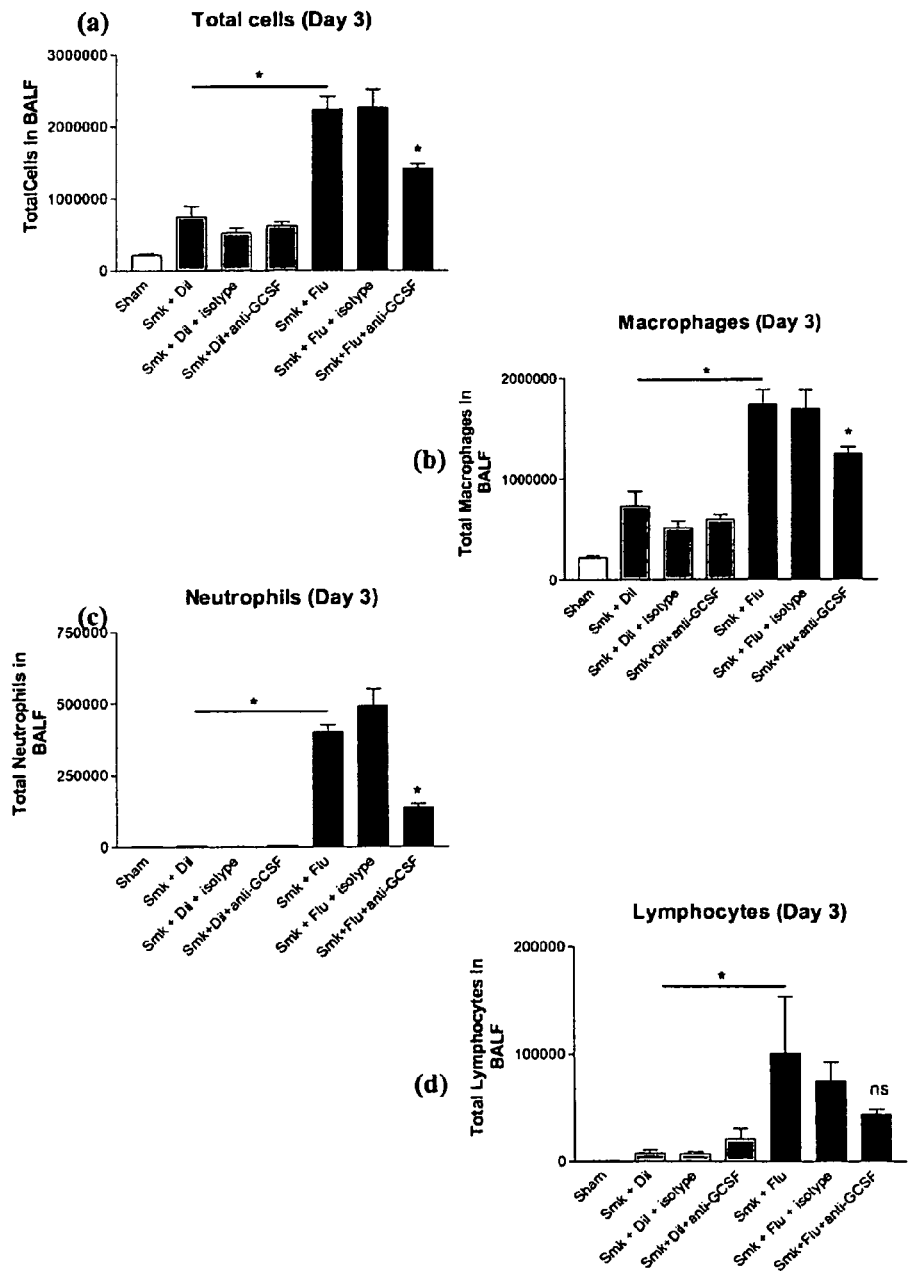
FIGS. 12a through d are graphical representations of total viable cells, macrophages, neutrophils and lymphocytes in BALF of influenza-treated, smoke-exposed mice after treatment with isotype or αG-CSFG-CSF antibody (Day 3 post-infection). The number of inflammatory cells in the BALF of control, influenza-treated+smoke-exposed and influenza+smoke+αG-CSFG-CSF antibody-treated animals was determined by standard differential cell analysis. Data are expressed as mean cells/mL BALF of eight animals per group±SEM. $P<0.05$ (annotated by *) are statistically significant, ns=not significant.

Effect of αG-CSF Antibody on Inflammatory Cell Number in BALF of Influenza-Treated and Smoke-Exposed Mice At Day 3 post-infection (FIG. 12), cigarette smoke-exposure caused a marked increase in the total number of cells (FIG. 12a) and numbers of macrophages (FIG. 12b) and lymphocytes (FIG. 12d) in BALF, which was further elevated, along with neutrophil number (FIG. 12c), by influenza infection of smoke-exposed mice.

The isotype control had no effect on total cell number or number of macrophages, neutrophils and lymphocytes in the BALF of smoke-exposed, influenza-treated mice.

αG-CSF, however, caused a significant reduction in the total number of cells and the number of macrophages and neutrophils, and a marked reduction in lymphocyte numbers in the BALF of smoke-exposed and influenza-treated animals.

Figure 13:
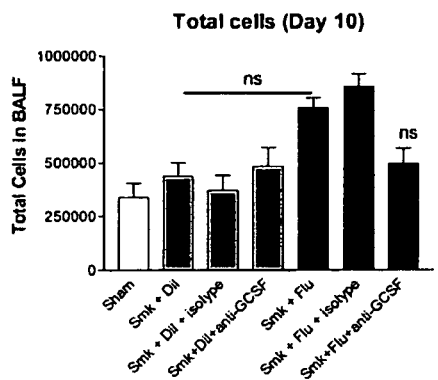
FIGS. 13a through d are graphical representations of total viable cells, macrophages, neutrophils and lymphocytes in BALF of influenza-treated, smoke-exposed mice after treatment with isotype or αG-CSFG-CSF antibody (Day 10 post-infection). The number of inflammatory cells in the BALF of control, influenza-treated+smoke-exposed and influenza+smoke+αG-CSFG-CSF antibody-treated animals was determined by standard differential cell analysis. Data are expressed as mean cells/mL BALF of eight animals per group±SEM. $P<0.05$ (annotated by *) are statistically significant, ns=not significant.
Figure 13:
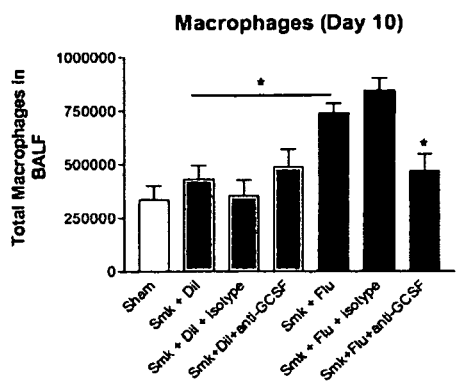
Figure 13:
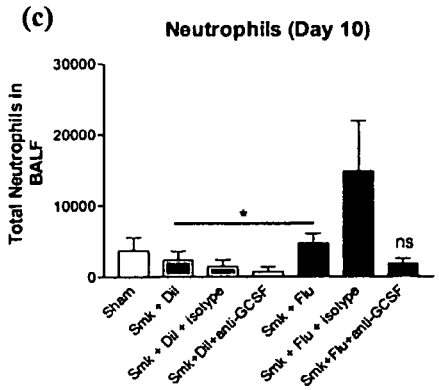
Figure 13:
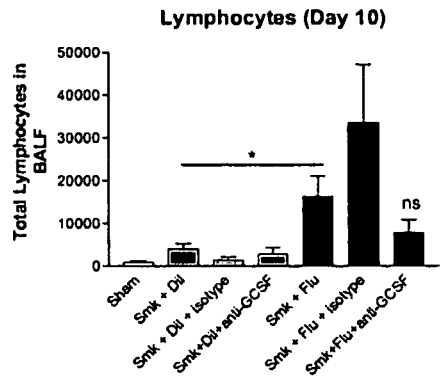

At Day 10 post-infection (FIG. 13), cigarette smoke exposure did not cause a marked increase in inflammatory cell number in the BALF. However, influenza-infection of smoke-exposed mice caused a marked increase in all inflammatory cells in the BALF (FIGS. 13a-d) which was slightly increased by isotype control, but markedly decreased by αG-CSF antibody treatment.

Figure 14:
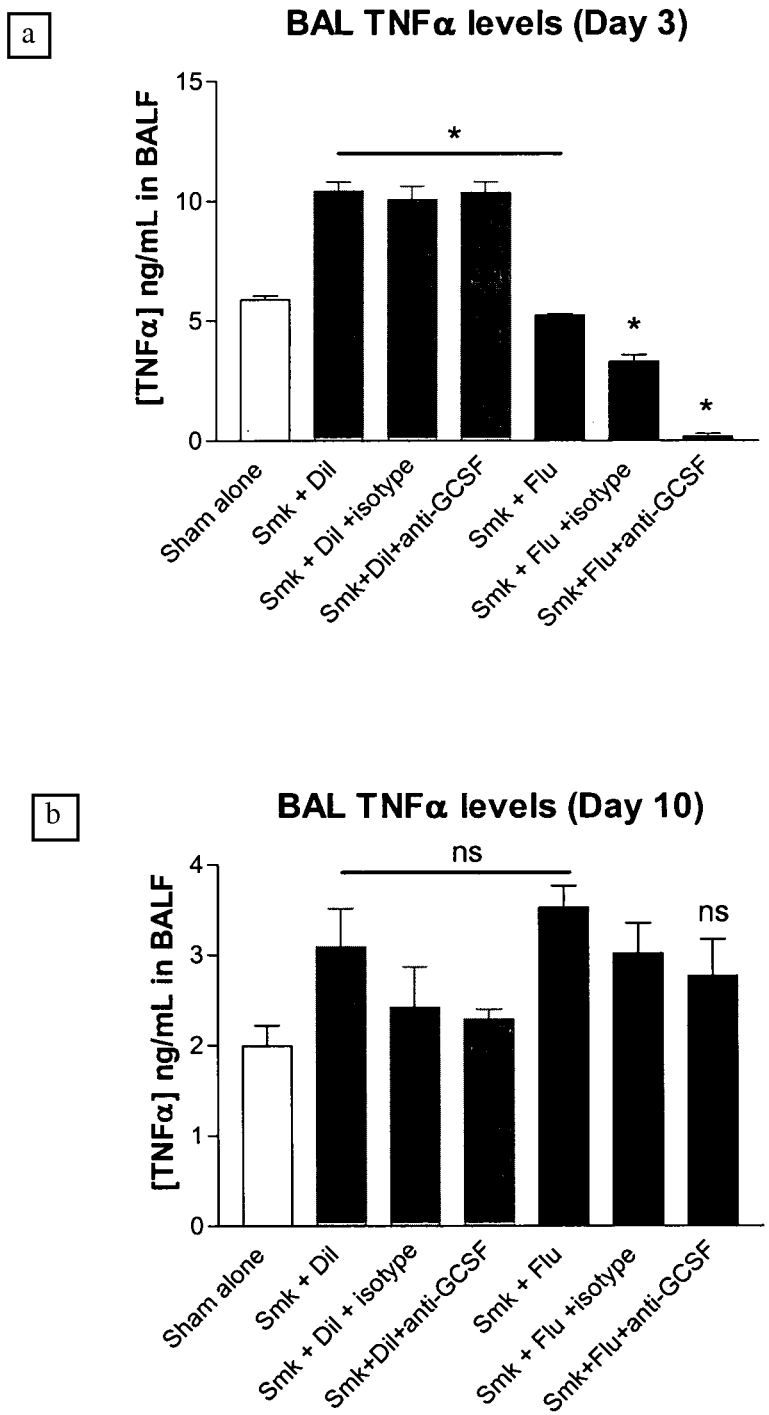
FIGS. 14 and *b* are graphical representations of protein levels of TNFα in BALF of influenza-treated, smoke-exposed mice after treatment with isotype or αG-CSFG-CSF antibody (Day 3 & 10 post-infection). The protein levels of TNFα in the BALF of control, influenza-treated+smoke-exposed and influenza+smoke+αG-CSFG-CSF antibody-treated animals were determined by ELISA. Data are expressed as the mean of eight animals per group±SEM. $P<0.05$ (annotated by *) are statistically significant, ns=not significant.

Effect of G-CSF Antibody on Protein Levels of TNFα, in BALF of Influenza-Treated and Smoke-Exposed Mice, as Determined by ELISAs Cigarette smoke exposure caused a marked increase in BALF TNFα levels at Day 3 and Day 10 (FIG. 14). Influenza caused a reduction in BALF TNFα at Day 3 post-infection which was further reduced by αG-CSF (FIG. 14a).

At Day 10 post-infection, influenza caused a small increase in BALF TNFα in smoke-exposed mice which was only slightly reduced by αG-CSF treatment (FIG. 14b).

The isotype control caused slight reductions in TNFα levels at both Day 3 and Day 10 which were not as marked as with αG-CSF antibody treatment.

Figure 15:
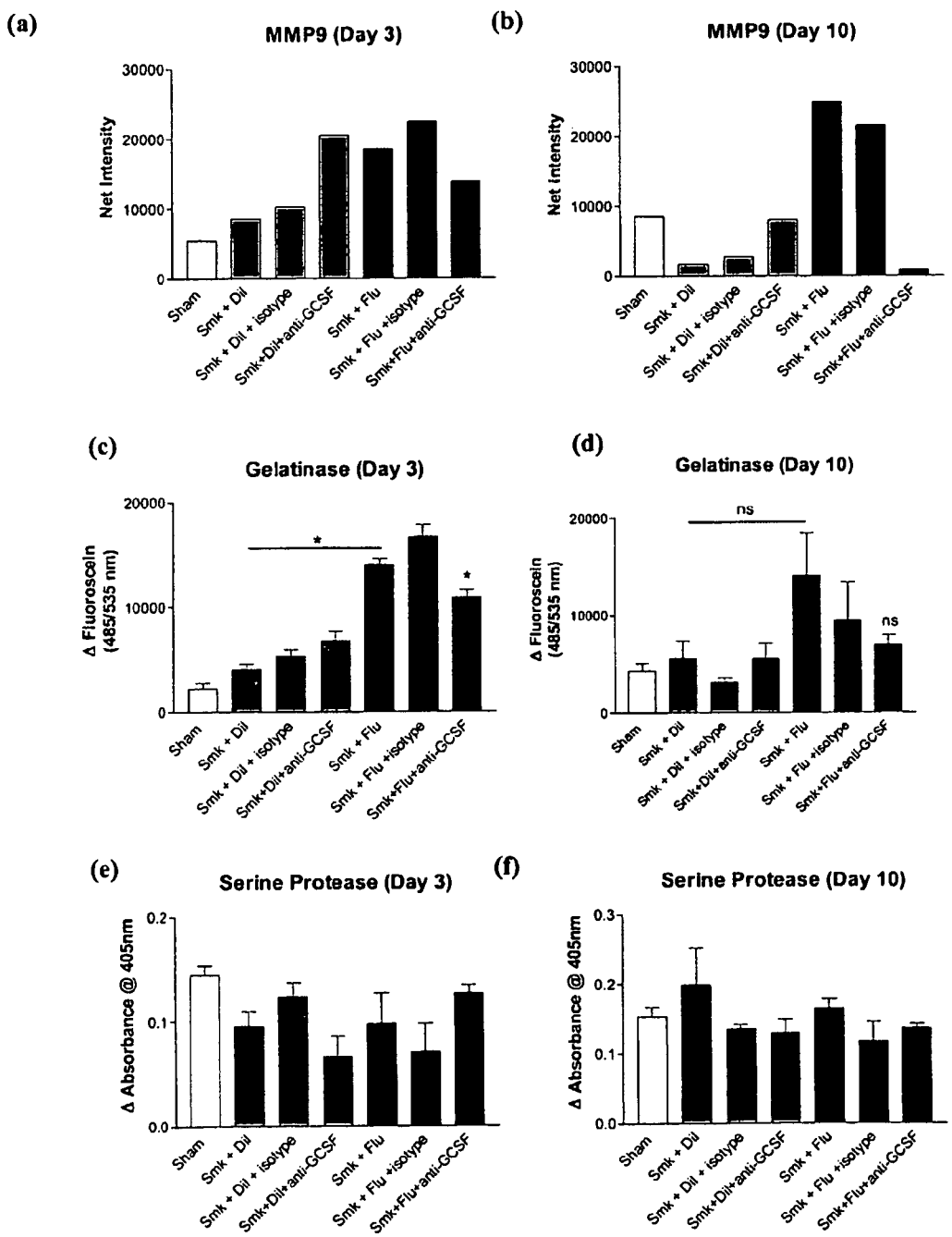
FIGS. 15*a* through *f* are graphical representations of MMP9 levels and protease activity in BALF of influenza-treated, smoke-exposed mice after treatment with isotype or αG-CSFG-CSF antibody (Day 3 & 10 post-infection). The levels of MMP9 in the BALF of control, influenza-treated+smoke-exposed and influenza+smoke+αG-CSFG-CSF antibody-treated animals were determined by zymography. Protease activity in the BALF of treated mice was determined by gelatinase and serine protease assay. Data are expressed as the pooled sample of eight mice per group and the mean of eight animals per group±SEM. $P<0.05$ (annotated by *) are statistically significant, ns=not significant.

Effect of αG-CSF Antibody on Protease Expression and Activity in BALF of Influenza-Treated and Smoke-Exposed Mice, as Determined by Zymography and Protease Assays At Day 3 post-infection, cigarette smoke caused a slight increase in MMP9 expression (FIG. 15a) and gelatinase activity (FIG. 15c). Gelatinase activity was further elevated with influenza infection. This elevation in protease levels and activity was reduced with αG-CSF treatment.

At Day 10 post-infection, cigarette smoke caused a reduction in MMP9 levels in BALF (FIG. 15b). Influenza infection increased MMP9 levels and gelatinase activity (FIG. 15c) in BALF of smoke-exposed mice at Day 10, and this elevation in protease levels and activity was reduced with αG-CSF.

There was no effect of either cigarette smoke exposure or influenza-infection on serine protease activity in BALF at Day 3 or Day 10 (FIGS. 15e and f) and, therefore, no discernable effect of αG-CSF.

Figure 16:
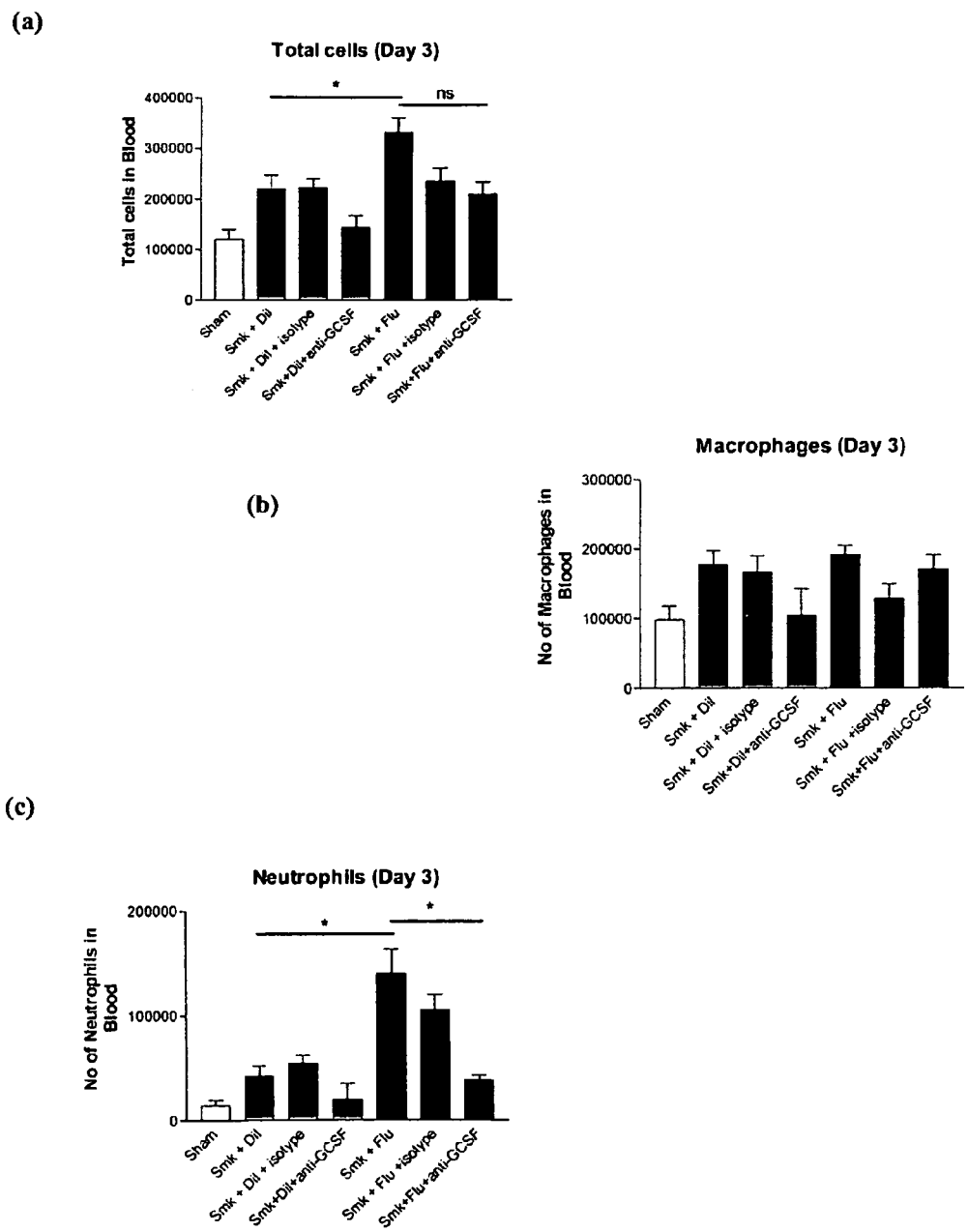
FIGS. 16*a* through *c* are graphical representations of total viable cells, macrophages and neutrophil in whole blood of influenza-treated, smoke-exposed mice after treatment with isotype or αG-CSFG-CSF antibody (Day 3 post-infection). The number of inflammatory cells in the BALF of control, influenza-treated+smoke-exposed and influenza+smoke+αG-CSFG-CSF antibody-treated animals was determined by standard differential cell analysis. Data are expressed as mean cells/mL BALF of eight animals per group±SEM. $P<0.05$ (annotated by *) are statistically significant, ns=not significant.

Effect of αG-CSF Antibody on Inflammatory Cell Number in Blood of Influenza-Treated and Smoke-Exposed Mice At Day 3 post-infection (FIG. 16), cigarette smoke caused a marked increase in inflammatory cells in the blood which was significantly increased after influenza exposure (macrophage numbers were markedly elevated after influenza infection). αG-CSF caused a significant reduction in neutrophil number in the blood of smoke-exposed and influenza-infected animals (FIG. 16c), and a marked reduction in total cell number in the blood. αG-CSF had little effect on macrophage number in the blood of smoke-exposed, influenza-infected mice.

Figure 17:
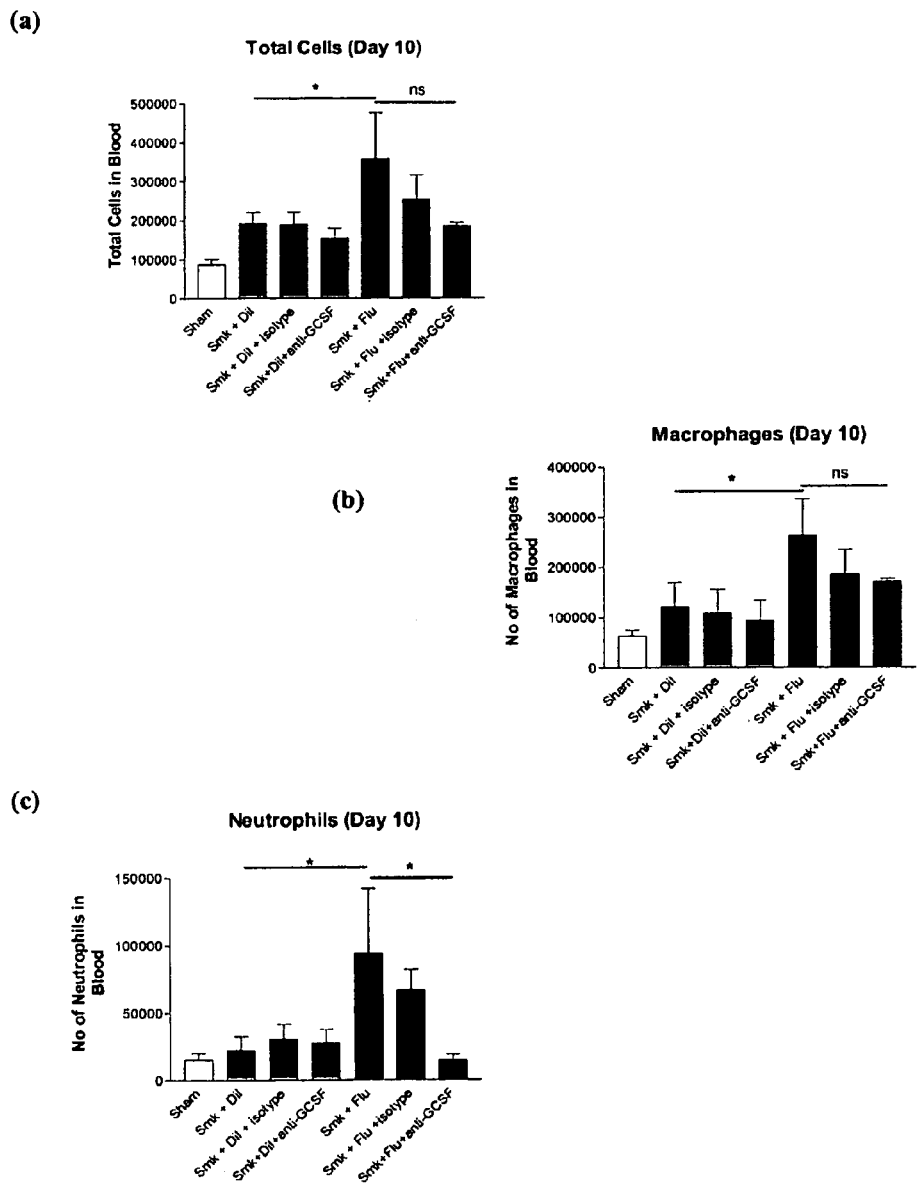
FIGS. 17*a* through *c* are graphical representations of total viable cells, macrophages and neutrophils in whole blood of influenza-treated, smoke-exposed mice after treatment with isotype or αG-CSFG-CSF antibody (Day 10 post-infection). The number of inflammatory cells in the BALF of control, influenza-treated+smoke-exposed and influenza+smoke+αG-CSFG-CSF antibody-treated animals was determined by standard differential cell analysis. Data are expressed as mean cells/mL BALF of eight animals per group±SEM. $P<0.05$ (annotated by *) are statistically significant, ns=not significant.

At Day 10 post-infection (FIG. 17), influenza infection caused a significant increase in total cell, macrophage and neutrophil numbers in the blood of smoke-exposed mice. αG-CSF caused a significant reduction in neutrophil number and a marked reduction in macrophage and total cell number in the blood of smoke-exposed and influenza-infected mice.

Figure 18:
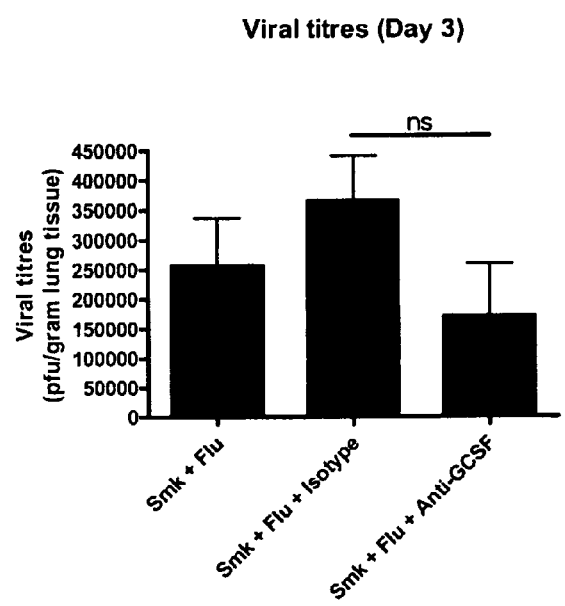
FIG. 18 is a graphical representation of viral titres in the lungs of control, influenza-treated+smoke-exposed and influenza+smoke+αGCSF antibody-treated animals determined by standard plaque assay titration. Data are expressed as the mean of 8 animals per group±SEM. ns=not significant.

Effect of αG-CSF Antibody on Viral Titres in the Lungs of Influenza-Treated and Smoke Exposed Mice αG-CSF caused a marked reduction in viral titres in smoke-exposed and influenza-infected mice, compared to isotype-treated mice (FIG. 18) at Day 3 post-infection. No virus was detected in any of the treatment groups at Day 10 post-infection.

Effect of αG-CSF Antibody on Inflammatory Cell Recruitment into the Lung Tissue of Influenza-Treated and Smoke-Exposed Mice, as Determined by Histological Analyses Samples were taken from the PFA-fixed lungs of control, influenza-treated+smoke-exposed and influenza+smoke+αG-CSF antibody-treated mice and paraffin-mounted and stained to reveal structural and cellular changes in lung parenchyma, vasculature and bronchi. Images were taken using a Zeiss microscope at 10× and 20×. Images taken at both Day 3 and Day 10 of a peribronchial region in the left lung showed that smoke and influenza caused marked potentiation of inflammation recognized as infiltration of the region between blood vessels and bronchus with mononuclear cells, neutrophils and lymphocytes. Parenchymal infiltration was also evident. In comparison to isotype control, the αG-CSF antibody markedly reduced the extent of inflammation in all regions.

EXAMPLE 4

Sub-Chronic Smoke

In this model, mice were exposed to smoke (or sham handled) 3 times a day (2 cigarettes/exposure) for 4 days, and analyzed on the fifth day, as previously described (Chen et al,

*Neuropsycho-pharmacology* 30(4):713-719, 2005). Mice were treated with either isotype control or 85 μg tn or 250 μg ip of anti-GCSF at t=d−1 and d+2.

Experimental Design:

Mice were exposed to cigarette smoke for 4 days, 3 times per day. Mice were treated with either isotype control (250 μg/dose ip or 85 μg/dose tn) or anti-GCSF (250 μg/dose ip or 85 μg/dose tn) at t=d−1 and d2, and then dissected on day 5. Smoke exposure conditions were as previously described (Vlahos et al, supra 2006). Briefly, mice received smoke from 3 cigarettes for 1 h and this was done three times per day for up to 4 days. Commercially available filter-tipped cigarettes (manufactured by Philip Morris, Australia) of the following composition were used: 16 mg or less of tar, 1.2 mg or less of nicotine and 15 mg or less of CO. Smoke was generated in 50 ml tidal volumes over 10 s using timed draw-back mimicking normal smoking inhalation volume and cigarette burn rate.

(i) Groups:
1. Sham (handled but no smoke exposure)
2. Smoke alone
3. Smoke+isotype via transnasal (85 μg=50 μL @ 1.7 mg/mL) (Rat IgG1, GL113)
4. Smoke+anti-GCSF via transnasal (85 μg=50 μL @ 1.7 mg/mL) (Rat anti-GCSF, MAB414)
5. Smoke+isotype via IP injection (250 μg) (Rat IgG1, GL113)
6. Smoke+anti-GCSF via IP injection (250 μg) (Rat anti-GCSF, MAB414)

(ii) Endpoints:
BAL fluid
   total/differential cell counts
   ELISAs (TNF alpha)
   zymography (protease induction)
Blood
   total/differential cell counts
Whole lungs
   snap-frozen and pooled for each group Note: The following graphs have been provided: graphs of BAL fluid and blood cell counts, graphs of ELISA results and zymography gels. Frozen BAL fluid samples and pooled lung samples will be shipped to the client.

(iii) Mice Required:
   8/group
   48 mice (iv) Drug Formulation:
Test compound: αG-CSF antibody
Specificity: mouse G-CSF (neutralises G-CSF bioactivity)
Ig class: rat IgG1
Source: R&D Systems
Catalog number: MAB414
Clone: 67604
Endotoxin level: <0.1 EU per 1 μg of mAb, as supplied by R&D.
Formulation: Supplied as a 0.2 μM filtered solution in PBS at 9.95 mg/mL.
Diluted to 1.0 mg/mL with sterile endotoxin free PBS: Provided as 5 mg (5 mL) aliquots, stored at −20° C.
Dosage: 250 μg/injection/mouse, i.p or 85 μg/transnasal/mouse, t.n.
Test compound: isotype control antibody
Specificity: *E. coli* β-galactosidase
Ig class: rat IgG1
Source: Walter and Eliza Hall Institute Monoclonal Antibody Lab
Clone: GL113
Endotoxin level: <0.1 EU per 1 μg of mAb, as supplied by WEHI.
Formulation: Supplied as a sterile solution in PBS at 1.3 mg/mL. Diluted to 1.0 mg/mL with sterile endotoxin free PBS. Provided in 5 mg (5 mL) aliquots; stored at −20° C.
Dosage: 250 μg/injection/mouse, i.p or 85 μg/transnasal/mouse, t.n.

Figure 19:
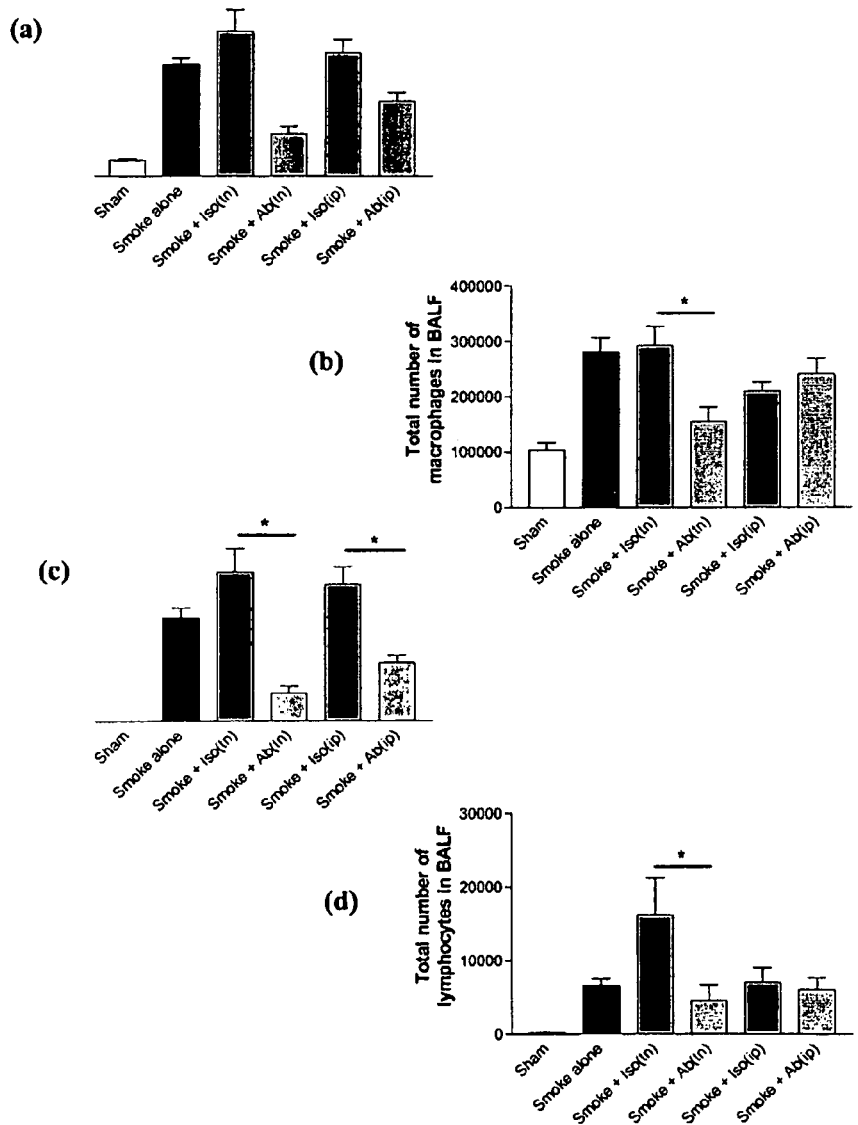
FIG. 19*a* through *d* are graphical representations of total viable cells, macrophages, neutrophils and lymphocytes in BALF of sham or smoke-exposed mice after treatment with isotype or αGCSF antibody. The number of inflammatory cells in the BALF of control, smoke-exposed and smoke+αGCSF antibody-treated animals was determined by standard differential cell analysis. Data are expressed as mean cells/mL BALF of eight animals per group±SEM. $P<0.05$ (annotated by *) are statistically significant, ns=not significant.

Effect of αG-CSF Antibody on Inflammatory Cell Number in BALF of Smoke-Exposed Mice 4-day smoke exposure caused a significant increase in total viable cells, macrophages, neutrophils and lymphocytes in BALF compared to the sham group (FIG. 19).

The αG-CSF antibody administered transnasally, caused a significant reduction in total viable cells, macrophages, neutrophils and lymphocytes in BALF compared to the transnasally-administered isotype group.

The αG-CSF antibody administered via intraperitoneal injection caused a significant reduction in total viable cells and neutrophils, but had no effect on macrophage or lymphocyte numbers, in the BALF compared to the isotype (ip) group.

EXAMPLE 5

Inhibition of G-CSF Mediated Proliferation in hG-CSF Receptor Expressing Ba/F3 Cells by Various G-CSF Antagonists BaF3 cells stably transfected with hG-CSFR as described by Layton et al, supra 1997 were cultured in 96 well plates at 20,000 cells/well in DMEM media with 5% FBS and 0.5 ng/ml rh or mGCSF (R&D Systems Cat #214-CS and Cat#414-CS respectively). G-CSF antagonists (R&D Systems MAB414, anti-hG-CSFR mAb711 and hG-CSFR-Fc) were added at threefold titrating doses starting from 1 μM and cell proliferation measured by MTS reduction (Cory et al, *Cancer Commun.* 3:207-12, 1991; Riss and Moravec, supra 1993) after 48 hours culture.

A. Inhibition by Anti-G-CSF Antibody:
A commercial R&D Systems antibody MAB414 was able to inhibit mG-CSF proliferation with an $IC_{50}$ of 10 μM.

B. Inhibition by Anti-hG-CSFR Antibody:
A murine monoclonal antibody against the hG-CSF Receptor, mAb711, (Layton et al, supra 1997) and its humanized derivative were able to inhibit mG-CSF proliferation with $IC_{50}$'s of 1.1 nM and 1.5 nM respectively.

A chimeric antibody comprising the heavy and light chain variable regions of mAb711 and human IgG1 heavy and light chain constant regions inhibited G-CSF activity with a similar $IC_{50}$ to the murine monoclonal antibody mAb711.

C. Inhibition by Soluble hG-CSFR-Fc Protein:
A soluble G-CSFR-Fc protein (Honjo et al, *Acta Cryst* F61:788-790, 2005) was able to inhibit mG-CSF proliferation with an $IC_{50}$ of 22 μM.

These results demonstrate that the biological activity of G-CSF may be inhibited by a variety of antagonists, including but not limited to antibodies to G-CSF, antibodies to G-CSFR, and soluble G-CSF receptors.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Ausubel et al. (eds.), *Current Protocols in Molecular Biology*, John Wiley & Sons, Inc.m 1994

Barnes, *N Engl J Med* 343(4):269-280, 2000
Barnes et al, *Eur Respir J* 22:672-688, 2003
Barnes, *Cytokine Growth Factor Rev* 14(6):511-522, 2003
Beeh and Beier, *Clin Exp Allergy* 26(2):142-157, 2006
Bird, *Science* 242:423, 1988
Bozinovski et al, *J Biol Chem* 277(45):42808-42814, 2002
Bozinovski et al, *Am J Physiol Lung Cell Mol Physiol* 286 (4):L877-885, 2004
Bozinovski et al, *J Proteome Res* 4(1):136-145, 2005
Brennan et al, *Science* 229:81, 1985
Bungart et al, *British Journal of Haematology* 22:1156, 1990
Carter et al, *Proc. Nat. Acad. Sci.* 89:4285 1992
Carter et al, *Bio/Technology* 10: 163-167, 1992
Chen et al, *Neuropsychopharmacology* 30(4), 713-719 2005
Clackson et al, *Nature* 352:624-628, 1991
Colotta et al, *Blood* 80:2012-2020, 1992
Cory et al, *Cancer Commun.* 3:207-212, 1991
de Haan et al, *Blood* 86:2986-2992, 1995
Demetri et al, *Blood* 78:2791-2808, 1991
Di Stefano et al, *Am J Respir Crit Care Med* 158(4):1277-1285, 1998
EP Patent No. 0 216 846
EP Patent No. 0 256 055
EP Patent No. 0 323 997
EP Patent Application No. 89303964.4
Geng et al, *Molecular Immunology* 44:5121-529, 2007
Gericke et al, *Journal of Leukocyte Biology* 57:455-461, 1995
Honjo et al, *Acta Crystallograph Sect F Struct Biol Cryst Commun.* 61 (Pt 8):788-90, 2005
Honjo et al, *Acta Cryst F*61:788-790, 2005
Huston et al, *Proc. Natl. Acad. Sci. USA* 85:5879, 1988
Jacob et al, *Blood* 92:353-361, 1998
Jones et al, *Nature* 321:522-525, 1986
Kabat et al. in *Sequences of Proteins of Immunological Interest*, 5th Ed., US Department of Health and Human Services, PHS, NIH, NIH Publication No. 91-3242, 1991
Keatings et al, *Am J Respir Crit. Care Med* 153(2):530-534, 1996
Kohler and Milstein, *Nature* 256:495-499, 1975
Kortt et al, *Protein Engineering* 10:423, 1997
Larrick et al, *Bio/Technology* 7:934, 1989
Layton et al, *J. Biol. chem.* 272:29735-29741, 1997
Layton et al, *Growth Factors* 14:117-130, 1997
Liu et al, *Proc. Natl. Acad. Sci. USA* 84:3439, 1987
Lopez and Murray, *Nat Med* 4(11):1241-1243, 1998
Lord et al, *Proc. Natl. Acad. Sci. USA* 86:9499-9503, 1989
Marks et al, *J. Mol. Biol.* 222:581-597, 1991
Morimoto et al, *Journal of Biochemical and Biophysical Methods* 24:107-117, 1992
Morrison et al, *Proc. Nat. Acad. Sci.* 81:6851, 1984
Nicola et al, *Journal of Biological Chemistry* 258:9017, 1983
Nicola et al, *Nature* 314:625, 1985
Metcalf, *International Journal of Cancer* 25:225, 1980
Padlan et al, *Mol. Immunol.* 28:489-498, 1991
Pedersen et al, *J. Mol. Biol.* 235:959-973, 1994
Pesci et al, *Eur Respir J.* 12(2):380-386, 1998
Presta, *Curr. Op. Struct. Biol.* 2:593-596, 1992
Reichmann et al, *Nature* 332:323-329, 1988
Retamales et al, *Am J Respir Crit Care Med* 164:469-473, 2001
Rex et al, *Transfusion* 35:605-611, 1995
Riss and Moravec, *Mol. Cell. Biol.* 3(1):184a, 1993
Roberts et al, *Blood* 89:2736-2744, 1997
Sambrook, Fritsch & Maniatis, *Molecular Cloning: A Laboratory Manual*, Second Edition (1989) Cold Spring Harbor Laboratory Press, Cold Spring Harbor, N.Y.; DNA Cloning: *A Practical Approach*, Volumes I and II, D.N. Glover ed. 1985
Sommerhoff et al, *J Clin Invest* 85(3):682-289, 1990
Souza et al, *Science* 232:61, 1986
Stanescu et al, *Thorax* 51(3):267-271, 1996
Stockely, *Am J Respir Crit Care Med* 160(5 Pt 2):S49-52, 1999
Stockley, *Chest* 121(5 Suppl):151S-155S, 2002
Summerton and Weller, *Antisense and Nucleic Acid Drug Development* 7: 187-195, 1997
Tomizuka et al, *Proc. Natl. Acad. Sci. USA* 97:722-727, 2000.
U.S. Pat. No. 4,399,216
U.S. Pat. No. 4,740,461
U.S. Pat. No. 4,816,567
U.S. Pat. No. 4,912,040
U.S. Pat. No. 4,946,778
U.S. Pat. No. 4,959,455
U.S. Pat. No. 5,223,409
U.S. Pat. No. 5,403,484
U.S. Pat. No. 5,427,908
U.S. Pat. No. 5,476,996
U.S. Pat. No. 5,571,698
U.S. Pat. No. 5,698,767
U.S. Pat. No. 5,580,717
U.S. Pat. No. 5,589,456
U.S. Pat. No. 5,939,598
U.S. Pat. No. 5,885,793
U.S. Pat. No. 5,969,108
U.S. Pat. No. 6,075,181
U.S. Pat. No. 6,114,598
U.S. Pat. No. 6,150,584
U.S. Pat. No. 6,162,963
U.S. Pat. No. 6,172,197
U.S. Pat. No. 6,521,404
U.S. Pat. No. 6,544,731
U.S. Pat. No. 6,555,313
U.S. Pat. No. 6,582,915
U.S. Pat. No. 6,593,081
Vlahos et al, *Am J Physiol Lung Cell Mol Physiol* 290(5):L931-945, 2006
Ward et al, *Nature* 334:544, 1989
Welte et al, *Blood* 88:1907-1929, 1996
Winter & Harris, *TIPS* 14:139, 1993
WO 1993/02108
WO 1999/55369
Xu et al, *British Journal of Haematology* 93:558-568, 1996
Yong et al, *European Journal of Haematology* 49:251-259, 1992
Yong, *British Journal of Haematology* 94:40-47, 1996
Youil, *J Virol Methods* 120(1):23-31, 2004

What is claimed is:

1. A method for treating chronic obstructive pulmonary disease (COPD) in a subject, said method comprising administering to said subject an antibody specific for G-CSFR in an amount sufficient to reduce one or more symptoms of COPD in said subject.

2. The method of claim 1, wherein the G-CSFR antibody is an antigen binding fragment specific for G-CSFR.

3. The method of claim 1 wherein the one or more symptoms are chosen from increased neutrophil infiltration, increased neutrophils in bronchoalveolar lavage fluid (BALF), increased neutrophils in sputum, declining lung function, and increased levels of serine proteases.

4. The method of claim 1 wherein the subject is a human.

5. The method of claim 1 further comprising the administration of a therapeutic agent selected from the list consisting of an anti-inflammatory agent, bronchodilator and an antibiotic.

6. The method of claim 1 wherein the antibody specific for G-CSFR is a monoclonal antibody.

7. The method of claim 6 wherein the antibody is a chimeric, human or humanized antibody.

8. The method of claim 6 wherein the antibody is a human antibody.

* * * * *